（12) United States Patent
Kechichian et al.

(10) Patent No.: US 11,630,120 B2
(45) Date of Patent: Apr. 18, 2023

(54) SYSTEM AND METHOD FOR DETECTING WRIST-DEVICE WEARING LOCATION

(71) Applicant: KONINKLIJKE PHILIPS N.V., Eindhoven (NL)

(72) Inventors: Patrick Kechichian, Eindhoven (NL); Warner Rudolph Theophile Ten Kate, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/197,244

(22) Filed: Mar. 10, 2021

(65) Prior Publication Data

US 2021/0349122 A1    Nov. 11, 2021

Related U.S. Application Data

(60) Provisional application No. 62/987,659, filed on Mar. 10, 2020.

(51) Int. Cl.
*G01P 15/08*  (2006.01)
*G01P 1/00*  (2006.01)
*G01P 13/00*  (2006.01)

(52) U.S. Cl.
CPC .............. *G01P 15/08* (2013.01); *G01P 1/00* (2013.01); *G01P 13/00* (2013.01)

(58) Field of Classification Search
CPC ............ G01P 15/08; G01P 1/00; G01P 13/00; A61B 5/6898; A61B 5/1118; A61B 5/1122; A61B 5/7235; A61B 5/7267; A61B 5/742; A61B 5/7475; A61B 5/681

USPC ........................................................ 73/865.4
See application file for complete search history.

(56) References Cited

U.S. PATENT DOCUMENTS

| 8,538,722 | B2 | 9/2013 | Naya |
| 10,282,155 | B2 | 5/2019 | Alberth, Jr. et al. |
| 10,467,679 | B1 * | 11/2019 | Toumazou ............ G06F 1/1694 |
| 2011/0109329 | A1 | 5/2011 | Diebold |
| 2016/0287180 | A1 * | 10/2016 | Ansari ................. A61B 8/5223 |
| 2017/0230754 | A1 | 8/2017 | Dusan |
| 2018/0172441 | A1 | 6/2018 | Hoque |
| 2018/0173483 | A1 | 6/2018 | Wang |
| 2019/0049479 | A1 * | 2/2019 | Malhotra ............... G06V 40/23 |
| 2019/0220069 | A1 | 7/2019 | Dusan |

FOREIGN PATENT DOCUMENTS

| CN | 110187759 A | 8/2019 |
| JP | 2017207848 A | 11/2017 |

OTHER PUBLICATIONS

International Search Report and Written Opinion, International Application No. PCT/EP2021/055505, dated Jun. 9, 2021.
Chew, K. et al., "Left and Right Hand Gesture Classification Using Scatter Diagram and Principle Component Analysis", 2012, IEEE.

* cited by examiner

*Primary Examiner* — Lee E Rodak
*Assistant Examiner* — Byung Ro Lee

(57) ABSTRACT

In one embodiment, an apparatus (12) that samples a signal obtained or derived from an accelerometer, filters the samples, accumulates the filtered samples, and determines which limb the apparatus is associated with based on a comparison of the filtered accumulated samples and a threshold set.

12 Claims, 9 Drawing Sheets

SYSTEM AND METHOD FOR DETECTING WRIST-DEVICE WEARING LOCATION

CROSS-REFERENCE TO PRIOR APPLICATIONS

This application claims the benefit of U.S. Provisional Application No. 62/987,659, filed on 10 Mar. 2020. This application is hereby incorporated by reference herein.

FIELD OF THE INVENTION

The present invention is generally related to wearable and hand-held devices, and in particular, wrist-worn wearable devices.

BACKGROUND OF THE INVENTION

Smartwatch devices worn on a user's wrist typically include a host of sensors, including an accelerometer, a gyroscope, and light-emitting diode (LED) sensors. Unlike the LED sensors, which measure a user's heart rate, orientation sensors, which include accelerometer and gyroscope sensors, are used to estimate a user's activity. For example, wrist rotations measured by the gyroscope may be combined with an accelerometer's estimate of the gravitational vector to determine whether a person is glancing at their smartwatch's display. More advanced algorithms for estimating a user's activity type, including walking, running, cycling, and gym training, may be developed using signals from these sensors at the wrist. In many cases, these algorithms use a different subset of internal parameters depending on the wearing location of the user (i.e., left or right wrist). In practice, the user may be prompted to determine his or her wearing location during an initial setup of the smartwatch. This setting may also be changed later by the user by updating the location in the settings menu of the smartwatch. Currently most, if not all smartwatches, do not provide automatic detection of the location of the smartwatch (e.g., wrist placement).

However, U.S. Patent Publication No. 2019/0220069 (hereinafter, the '069 publication) describes an electronic device that can be worn on a limb of a user and that can include a processing device and one or more position sensing devices operatively connected to the processing device (see, Abstract). The processing device can be adapted to determine which limb of the user is wearing the electronic device based on one or more signals received from at least one position sensing device (see, Abstract). For instance, FIGS. 8 and 9 of the '069 publication show plots of signals measured along the x-axis, y-axis, and z-axis, and paragraph [0046] observes in part that plot 802 (pertaining to the accelerometer y-axis), when the electronic device 400 is worn on the right wrist, has a value of y at the first position 402 of substantially plus one and that when comparing plot 802 to plot 902 pertaining to the accelerometer y-axis (where the device 400 is worn on the left wrist), the value of y at the third position 402 is substantially minus one. Paragraph [0046] also notes that one or more of the plots shown in FIG. 8 or FIG. 9 can be analyzed to determine which limb of a user is wearing the electronic device.

SUMMARY OF THE INVENTION

One object of the present invention is to develop an apparatus that enables a determination as to which limb the apparatus is associated without consuming too many resources. To better address such concerns, in a first aspect of the invention, an apparatus that samples a signal obtained or derived from an accelerometer, filters the samples, accumulates the filtered samples, and determines to which limb the apparatus is associated based on a comparison of the filtered accumulated samples and a threshold set. By filtering the samples used in the limb association determination, the invention operates on a reduced data set and thus conserves processing power/memory resources.

In one embodiment, each sample of the plurality of samples is filtered based on at least a first threshold, and a processor of the apparatus is configured to isolate distribution tails of the signal obtained or derived from the accelerometer via the filtering based on the at least first threshold, wherein the at least first threshold corresponds to a gravitational norm value plus a predefined margin. The margin is chosen as a value sufficient to capture the relevant samples in the tail of the acceleration distribution. Thus, only values with magnitude that fall outside of a range determined by a threshold above a gravitational norm value (e.g., a threshold above 9.81 m/s$^2$) are accumulated, which may be viewed, and referred to herein, as a pre-filtering step. An advantage of such a first threshold is that sample values attributed to non-related activities are excluded from the estimation procedure, which reduces data processing and filters out data that may corrupt or otherwise reduce the accuracy of the determination results.

In one embodiment, the processor is further configured to filter the samples according to further a fourth threshold, wherein each sample that is greater than the first threshold and less than the fourth threshold comprises one of the filtered accumulated samples. The first threshold may be supplemented with an upper bound on the acceleration to isolate common human activity patterns and movements, excluding spurious wrist impacts, which again, reduces the data and hence data processing resources needed to process the data.

In one embodiment, the apparatus further comprises a user interface, wherein the processor is further configured to determine that the location of the apparatus has changed, and prompt a user to provide an indication of whether the apparatus is associated with the left limb or the right limb (e.g., left or right wrist, lower left or lower right leg, left or right hand). The apparatus further bolsters accuracy by confirming whether the limb association (e.g., to which limb is the apparatus held or secured) has changed.

In one embodiment, the apparatus comprises a wrist-worn device, wherein the accumulated samples are for a single axis of the accelerometer, and the processor is further configured to determine that the wrist-worn device is either located on a left wrist or a right wrist when a watchcase of the wrist-worn device is rotated by accumulating additional samples from another axis of the accelerometer to derive a second value and comparing signs of the first and second values, and determine that the wrist-worn device is located on the left wrist if the signs are equal, otherwise, determine that the wrist-worn device is located on the right wrist if the signs are not equal. For instance, wrist-worn devices may be unable to accurately assess wrist placement where the watchcase is rotated while being worn on the wrist. This scenario may be the case especially for smartwatches featuring a physical crown. For some users, the protruding crown may be uncomfortable due to pressing against the hand, and therefore options to rotate the entire case so that the crown faces away from the hand may be desired. The wrist-worn device provides a solution to determining the wrist location while being agnostic to the actual watchface rotation, providing an accurate determination of wrist placement.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Figure 1:
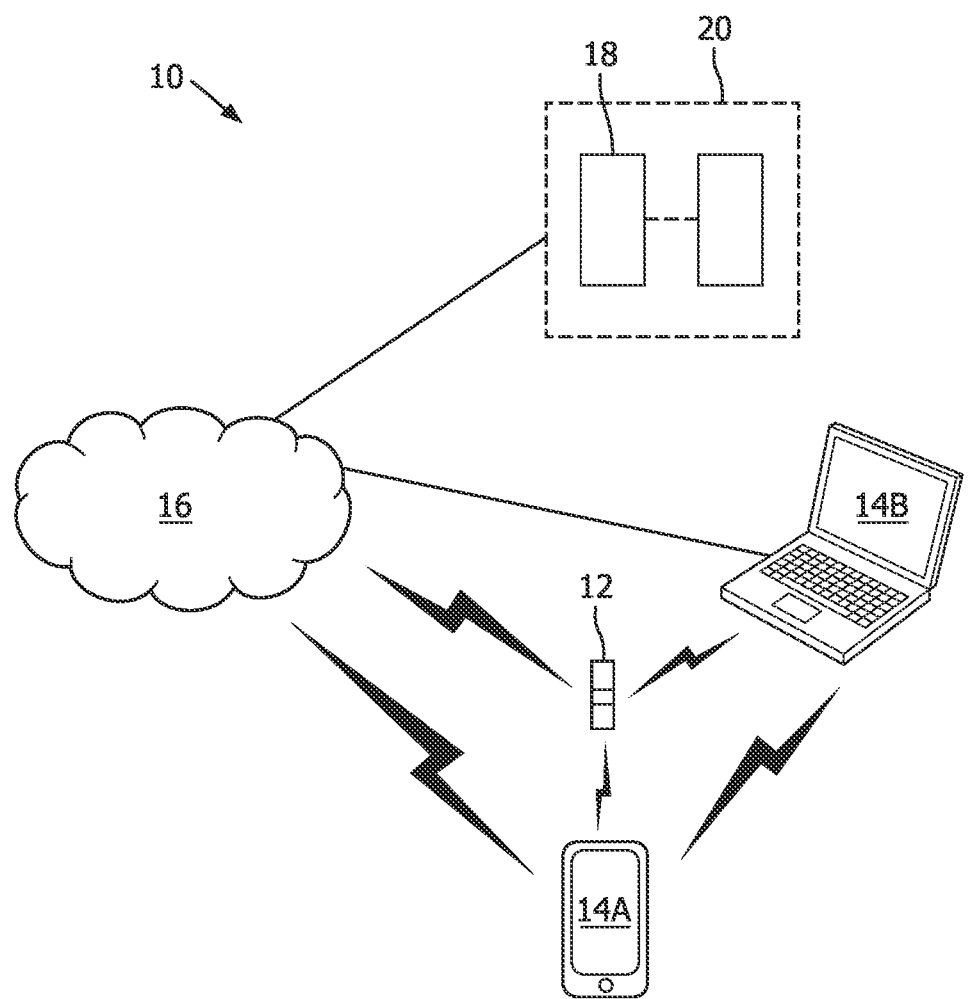
FIG. 1 is a schematic diagram that illustrates an example environment in which a wrist-worn device may be implemented, in accordance with an embodiment of the invention.

Disclosed herein are certain embodiments of an apparatus and associated method and computer program product (e.g., non-transitory computer readable medium) that determines to which limb the apparatus is associated. For instance, in the case of a wrist-worn device, the association determination refers to a determination of a wearing location (placement) of the wrist-worn device, including a smartwatch, using filtered, accumulated samples derived or obtained from one (e.g., single) axis of an accelerometer signal. As another example, the association determination refers to a determination of lower-limb wearing location (e.g., placed on a left or right lower limb) of the apparatus. As a further example, the association determination refers to a determination of which hand is carrying the apparatus. In one embodiment, the apparatus comprises a single or multi-axis accelerometer and one or more processors configured to sample a signal obtained or derived from the accelerometer, filter the resultant samples according to at least a first threshold, accumulate those filtered samples, and compare a value (or values in some embodiments) of the filtered accumulated samples to a threshold set. The threshold set may comprise plural (e.g., two) signed threshold values, or a single threshold value and a sign component (e.g., +/−). In one embodiment, the apparatus determines the limb association (e.g., wrist-worn location, lower limb-worn location, hand location) based on whether the value is greater than a threshold value (>P for the right limb) or less than a negative of the threshold value (<−P for the left limb). In some embodiments, limb location may be determined based on equality of signs using two axes. The use of the various thresholds may improve accuracy in the determined limb location by mitigating the risk of undesired yet captured or detected movements while reducing the burden on computational resources by, for instance, limiting the data set.

In the description that follows, emphasis is placed on an apparatus comprising a wrist-worn device for ease of discussion and illustration, with the understanding that a similar description applies for an apparatus configured as a lower limb-worn device or hand-held (hand-carried) device.

Digressing briefly, the aforementioned '069 publication reveals that one of the axes of the accelerometer may exhibit asymmetry between left and right wrist placement, though there does not appear to be any method disclosed that uses a technology that filters the samples to enable an accurate and/or efficient wrist location determination. Further, as indicated above, some systems may prompt a user for the wearing location, which may suffice when the user substitutes his or her normal everyday watch with a wrist-worn device such as a smartwatch, since its wearing location does not normally change. However, for wrist-worn devices that serve as health devices that may be worn for approximately twenty-four (24) hours a day, including fall detectors or other devices that continuously track a physiological state for a person at risk, a user typically switches the location of the device due to discomfort from prolonged wearing, especially the elderly with increased sensitivity to skin abrasion or bruising.

Some wrist-worn devices comprise algorithms related to classifying user activity, which may require wrist location information to track his or her health over time (e.g., for life-critical systems, such as automatic fall detection systems, where the consequences of missing a true fall episode may lead to death). Such algorithms often rely on detecting orientation changes of the wrist as part of their feature set, and therefore, knowledge about the device wearing location is important. For example, the impact experienced by a device may be less for when the device is worn on the right wrist and yet the user falls on his or her left side. For instance, for wrist-worn devices in fall detection, there is an inherent asymmetry in the types of impacts measured by the device accelerometer for sideways falls (e.g., whether the person falls on the arm that is wearing the device). That is, knowing the wearing location may make it easier to detect sideways falls (and adjust fall thresholds accordingly). Ultimately, determining the wearing location typically requires exploiting some asymmetry in the sensor data distributions, which is evidenced to some degree in the '069 publication.

One drawback to one or more of the aforementioned approaches is the heavy reliance on classifier or histogram based approaches. Classifiers require pre-training, which may further require an extensive amount of training/test data, and may be computationally expensive for detecting complex gestures. Histogram-based methods also require a large amount of data (and typically make use of all the data), and therefore there is a long delay before the correct wearing location can be estimated. Further, one disadvantage of using gestures to detect a wearing location is that detection typically requires additional sensor modalities, such as a gyroscope, magnetometer, or an air pressure sensor, which is more costly in terms of power. Gestures may also not occur as frequently in practice, and are not usually tied to higher fall-risk activities like walking. In certain embodiments of a wrist-worn device, the filtering (or also referred to herein as pre-filtering) of a sampled signal that is obtained or derived from a single accelerometer axis achieved via one or more thresholds for accumulating filtered samples serves to reduce the cost and/or complexity of the wrist-worn device, while conserving computational resources (e.g., due to a reduced data set). In some embodiments, sampling of an additional accelerometer axis may be implemented to ensure an accurate determination of wrist placement regardless of whether a watchface is rotated.

As noted above, in many cases, algorithms of wrist-worn devices use a different subset of internal parameters depending on the wearing location of the user. Certain features, such as a user's body rotation and arm extension are more or less pronounced depending on the wrist-wearing location (e.g., during a fall). For example, in the case of fall detection, an important feature is the change in height during the fall event (which should be downwards in case of a fall). Since measurements take place at the wrist for a wrist-worn device, the physical height change of the wrist might differ from the height change of the body (e.g., measured at the shoulder), which may introduce a larger variation in possible height changes and hence a reduction in the accuracy of the detector. One mechanism to account for this is by measuring the direction in which the arm is pointing before and after the event. For instance, in general, pointing upwards suggests the wrist is above the shoulder, whereas pointing downwards suggests the wrist is below the shoulder. Using the pointing direction enables an estimate of the height change the shoulder is conducting. Another parameter that may be used is the change in height by the wrist itself, such as determining whether the wrist is upwards of downwards (relative to body/shoulder). For a fall, an upwards orientation of the wrist is most likely. The pointing direction may be estimated using the direction at which gravity appears in the accelerometer signal. The wrist wearing location, as well as the flipping of the crown of the watchface, may affect the sign of the measured gravity. For at least these reasons, knowledge of the wearing location for the wrist-worn device is needed.

Another example concerns the orientation of the watch itself before and after the fall. For the same sign effect of gravity, one should account for the wearing location. There are other applications where the same problem may be present. Examples include gesture control and activity classification. In general, a problem arises when the orientation of the sensor with respect to the body (e.g., the arm) is relevant to determine the quantity of interest. Certain embodiments of a wrist-worn device are disclosed that are low-cost, do not require classifying gestures or activities, and only require a single axis of the accelerometer sensor to determine whether the device is worn on the left or right wrist. Furthermore, the wrist-worn device according to various embodiments disclosed herein requires fewer relevant samples to make a correct estimate of the wearing location.

Having summarized certain features and benefits of an apparatus of the present disclosure, reference will now be made in detail to the description of a wrist-worn device as illustrated in the drawings. While an apparatus will be described in connection with these drawings, there is no intent to limit the apparatus to the embodiment or embodiments disclosed or emphasized herein. For instance, though functionality for determining the limb association for the apparatus is described below as residing in the apparatus, in some embodiments, other devices may perform the limb-placement determinations and communicate the results to the apparatus, including where the decision-making resides in a local electronic device in communication with the apparatus and/or remote devices coupled via one or more networks to the apparatus. As another example, and as mentioned above, emphasis is placed on an apparatus configured as a wrist-worn device, though in some embodiments, the methods employed for the wrist-worn devices may similarly be employed for smartwatches, communications devices, gaming devices/apparatus, etc., worn around the lower limbs and/or held in one's hand (e.g., cellular phone, gaming apparatus, etc.). Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents consistent with the disclosure as defined by the appended claims. Further, it should be appreciated in the context of the present disclosure that the claims are not necessarily limited to the particular embodiments set out in the description.

Note that the description herein that refers to a determination of limb association or the like (e.g., wrist wearing location (left or right), lower limb wearing location (left or right), hand carrying location (left or right)) and that is performed according to one or more apparatus functionality includes inferences based on the receipt of certain signals or, in general, input or patterns of input.

Referring now to FIG. 1, shown is an example environment 10 in which certain embodiments of an apparatus configured as a wrist-worn device 12 may be implemented. It should be appreciated by one having ordinary skill in the art in the context of the present disclosure that the environment 10 is one example among many, and that some embodiments of a wrist-worn device 12 may be used in environments with fewer, greater, and/or different components than those depicted in FIG. 1. The environment 10 comprises a plurality of devices that enable communication of information throughout one or more networks. The depicted environment 10 comprises the wrist-worn device 12, one or more electronics devices 14 (e.g., 14A, 14B), a network 16, and one or more remote computing devices (e.g., computing and/or communication devices) 18. In one embodiment, the one or more computing devices 18 may include storage, computational resources, and communication functionality of a personal emergency response system (PERS) service facility 20, which may be used by agents (personnel) of the facility to assist a user or users of the personal emergency response system. That is, the facility personnel may receive alerts from the wrist-worn devices 12 and/or electronics devices 14 that indicate that a user has fallen or has experienced additional or another emergency situation, the personnel contacting the appropriate emergency personnel and/or designated caregivers and/or family members. In some embodiments, the facility may be comprised of a third party service, including providing health monitoring and/or coaching services for a user, among other services. In some embodiments, additional service facilities may be included in the environment 10. In the description that follows, a PERS environment is used as an example environment 10 in which the wrist-worn device 12 may be used, with the understanding that additional and/or other services may be used.

The wrist-worn device 12 is typically worn by a user (e.g., around the wrist in the form of a smartwatch, strap, or band-like accessory). In some embodiments, an apparatus comprising similar functionality may be strapped to a lower limb of the user or hand-carried. In one embodiment, the wrist-worn device 12 comprises one or more processors, a plurality of sensors, a communications module, a position location module (e.g., GPS module), a cellular/wireless module, and a rechargeable battery, among other components. The sensors of the wrist-worn device 12 comprise a single or multi-axis accelerometer (e.g., using piezoelectric, piezoresistive or capacitive technology in a microelectro-mechanical system (MEMS) infrastructure) for the detection of the wrist to which the wrist-worn device 12 is placed, the accelerometer also used in some embodiments for the prevention/detection of falls. The sensors of the wrist-worn device 12 may also include capacitive or proximity sensors for detecting when the wrist-worn device 12 is placed on the wrist. Communication functionality of the wrist-worn device 12 may include cellular and/or wireless communication functionality to enable local communication with the electronic devices 14 and/or remote communications with the one or more computing devices 18.

In one embodiment (e.g., for a PERS environment), the wrist-worn device 12 comprises wrist-location determination software, and/or fall detection software or other emergency assist software that receives an indication of an emergency event (e.g., either detected autonomously based on the use of one or more sensors and/or via a user depressing a button or other input on the wrist-worn device 12 or other devices) and responsively triggers an action at (e.g., sends an alert to) the one or more computing devices 18 of the PERS facility 20 or other devices (e.g., to a family member, friend, third party, or other caregiver). An agent at the PERS facility 20 can assist the user by contacting, on behalf of the user, emergency personnel and/or other designated caregivers. Communication between the wrist-worn device 12 and the PERS facility 20 may be achieved via the network 16, which may include one or any combination of a cellular network, a wireless network (e.g., Wireless Fidelity or Wi-Fi, 802.11, Bluetooth, Zigbee, etc.), and a local and/or wide area network and/or other networks. In one embodiment, the wrist-worn device 12 communicates with the PERS facility 20 directly (e.g., using cellular modem functionality) or via an intervening communication through one or more of the electronics device 14.

The electronics devices 14 may be embodied as a smartphone (e.g., 14A), mobile phone, cellular phone, smartwatch, pager, stand-alone image capture device (e.g., camera), laptop (e.g., 14B), tablet, workstation, smart glass (e.g., Google Glass™), hearing aid, virtual reality device, augmented reality device, gaming device, among other handheld and portable computing/communication devices. In some embodiments, the electronics device 14A may include at least some of the functionality of the wrist-worn device 12, and/or serve as a communications gateway to other devices (e.g., the remote computing devices 18). For instance, using functionality described herein for the wrist-worn device 12, the electronics device 14A (or the electronics device 14B that has an apparatus tethered to or otherwise coupled to the electronics device 14B, such as a gaming device) may likewise include an accelerometer (or similarly, an accelerometer in the gaming device) and software to enable the electronics device 14A,14B to determine which hand possesses the electronics device 14A. In some embodiments, one or more of the electronics devices 14 are not necessarily readily portable or even portable. For instance, the electronics device 14 may be a home appliance, including a refrigerator, microwave, oven, pillbox, home monitor, or stand-alone home virtual assistant device. In any event, the electronic devices 14 may be communicatively coupled to the wrist-worn device 12, to each other, and/or to the computing devices 18 of the PERS facility 20 via the network 16 (which may include a home Internet connection, telephony network, cable network, wireless network, local area network, Bluetooth network, Zigbee network, etc.). In some embodiments, the electronics device 14 may be a vehicle appliance (e.g., the automobile navigation system or communication system). In the depicted embodiment of FIG. 1, the electronics device 14A is embodied as a smartphone and the electronics device 14B is embodied as a laptop, with further discussion below for each.

In one embodiment, the smartphone 14A comprises at least two different processors, including a baseband processor and an application processor. The baseband processor comprises a dedicated processor for deploying functionality associated with a protocol stack, such as a GSM (Global System for Mobile communications) protocol stack. The application processor comprises a multi-core processor for providing a user interface and running applications, including in some embodiments, application software to receive sensor input (e.g., single or multi-axis accelerometer signals, capacitive or proximity sensor signals, etc.) and determine which hand is holding the smartphone 14A. The baseband processor and application processor have respective associated memory (e.g., random access memory (RAM), Flash memory, etc.), peripherals, and a running clock.

More particularly, the baseband processor may deploy functionality of a GSM protocol stack and/or a wireless communications module to enable the smartphone 14A to access one or a plurality of wireless network technologies, including WCDMA (Wideband Code Division Multiple Access), CDMA (Code Division Multiple Access), EDGE (Enhanced Data Rates for GSM Evolution), GPRS (General Packet Radio Service), Zigbee (e.g., based on IEEE 802.15.4), Bluetooth, Wi-Fi (Wireless Fidelity, such as based on IEEE 802.11), and/or LTE (Long Term Evolution), among variations thereof and/or other telecommunication protocols, standards, and/or specifications. The baseband processor manages radio communications and control functions, including signal modulation, radio frequency shifting, and encoding. The baseband processor may comprise a GSM modem having one or more antennas, a radio (e.g., RF front end), and analog and digital baseband circuitry. The RF front end comprises a transceiver and a power amplifier to enable the receiving and transmitting of signals of a plurality of different frequencies, enabling access to the network 16. The analog baseband is coupled to the radio and provides an interface between the analog and digital domains of the GSM modem. The analog baseband comprises circuitry including an analog-to-digital converter (ADC) and digitalto-analog converter (DAC), as well as control and power management/distribution components and an audio codec to process analog and/or digital signals received from the smartphone user interface (e.g., microphone, earpiece, ring tone, vibrator circuits, etc.). The ADC digitizes any analog signals for processing by the digital baseband processor. The digital baseband processor deploys the functionality of one or more levels of the GSM protocol stack (e.g., Layer 1, Layer 2, etc.), and comprises a microcontroller (e.g., microcontroller unit or MCU) and/or a digital signal processor (DSP) that communicate over a shared memory interface (the memory comprising data and control information and parameters that instruct the actions to be taken on the data processed by the application processor). The MCU may be embodied as a RISC (reduced instruction set computer) machine that runs a real-time operating system (RTIOS), with cores having a plurality of peripherals (e.g., circuitry packaged as integrated circuits) such as RTC (real-time clock), SPI (serial peripheral interface), I2C (inter-integrated circuit), UARTs (Universal Asynchronous Receiver/Transmitter), devices based on IrDA (Infrared Data Association), SD/MMC (Secure Digital/Multimedia Cards) card controller, keypad scan controller, and USB devices, GPRS crypto module, TDMA (Time Division Multiple Access), smart card reader interface (e.g., for the one or more SIM (Subscriber Identity Module) cards), timers, and among others. For receive-side functionality, the MCU instructs the DSP to receive, for instance, in-phase/quadrature (I/Q) samples from the analog baseband and perform detection, demodulation, and decoding with reporting back to the MCU. For transmit-side functionality, the MCU presents transmittable data and auxiliary information to the DSP, which encodes the data and provides to the analog baseband (e.g., converted to analog signals by the DAC). The application processor may be embodied as a System on a Chip (SOC), and supports a plurality of multimedia related features including web browsing to access one or more computing devices 18 of the PERS facility 20 and/or other service facilities that may be used for multimedia entertainment, games, etc.

The application processor generally comprises a processor core (Advanced RISC Machine or ARM), multimedia modules (for decoding/encoding pictures, video, and/or audio), a graphics processing unit (GPU), wireless interfaces, and device interfaces. The application processor includes an operating system that enables the implementation of a plurality of user applications. For instance, the application processor may deploy interface software (e.g., middleware, such as a browser with or operable in association with one or more application program interfaces (APIs)) to enable access to a cloud computing framework or other networks to provide remote data access/storage/processing, and through cooperation with an embedded operating system, access to calendars, location services, reminders, etc. In one embodiment, the application processor may run application software (e.g., executable code or instructions) that determines which hand is carrying the smartphone 14A. In some embodiments, the application software may receive sensor input from sensors (e.g., contact sensors, accelerometers, etc.) located in the smartphone 14A, process the signals to determine at least which hand is carrying the smartphone, and communicate the results to the user and/or other devices for storage and/or further processing. In some embodiments, one or more of the processing for the smartphone 14A may be implemented in another device (e.g., the other electronics device 14B, the wrist-worn device 12, and/or the remote computing devices 18). For instance, the smartphone 14A may offload the determination of which hand is carrying the smartphone 14A to the remote computing device 18 (e.g., when compute resources of the smartphone 14A are incapable of performing the processing, such as due to insufficient memory or battery charge). In some embodiments, the smartphone 14A may perform one or more of the wrist-location determination functionality of the wrist-worn device 12, such as when the wrist-worn device 12 lacks the capability (e.g., due to insufficient charge and/or processing resources) to perform such functions. In these embodiments, the wrist-worn device 12 may communicate the accelerometer sensor input (and/or other sensor input) to the smartphone 14A, the smartphone 14A may perform the wrist placement processing, and then the smartphone 14A communicates the results of the processing via its own screen display and/or to the wrist-worn device 12 for presentation to a user.

The wireless interfaces of the smartphone 14A may include Bluetooth and/or Zigbee module(s), among others, that enables wireless communication with the wrist-worn device 12 or other local devices, a wireless fidelity (Wi-Fi) module for interfacing with a local 802.11 network, and/or a GSM module for access to a cellular/wireless component of the network 16 and communication to other devices. The device interfaces coupled to the application processor may include a respective interface for such devices as a display screen. The display screen may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), or retina or haptic-based technology. For instance, the display screen may be used to present prompts to the user (e.g., confirming which hand is carrying the smartphone 14), among other visualizations. Other interfaces include a keypad, USB (Universal Serial Bus), SD/MMC card, camera, among other devices.

The laptop 14B may be in wireless or wired communication with the other devices 12, 14A, 18. For instance, the wired connection may be temporary, such as via USB connection, or persistent, such as an Ethernet connection. The laptop 14B may include similar hardware and software/firmware to that described above for the smartphone 14A to enable access to wireless and/or cellular networks (e.g., through communication cards comprising radio and/or cellular modem functionality) and/or other devices (e.g., Bluetooth transceivers, NFC transceivers, etc.), such as wireless or (temporary) wired connection to the wrist-worn device 12. In some implementations, the laptop 14B may be coupled to the remote computing devices 18 via plain old telephone service (POTS), using technologies such as digital subscriber line (DSL), asymmetric DSL (ADSL), and/or according to broadband technology that uses a coaxial, twisted pair, and/or fiber optic medium. Discussion of such communication functionality is omitted here for brevity. Generally, in terms of hardware architecture, the laptop 14B includes a processor, memory, and one or more input and/or output (I/O) devices (or peripherals) that are communicatively coupled via a local interface. The local interface can be, for example but not limited to, one or more buses or other wired or wireless connections. The local interface may have additional elements, which are omitted for brevity, such as controllers, buffers (caches), drivers, repeaters, and receivers, to enable communications. Further, the local interface may include address, control, and/or data connections to enable appropriate communications among the aforementioned components. Peripherals coupled to the laptop 14B may include a gaming apparatus with sensors (e.g., accelerometer, proximity sensors, etc.), which may feed data to the laptop 14B for determination of limb placement as similarly described above.

The processor or processors of the laptop 14B may comprise hardware for executing software, particularly that stored in memory. The processor(s) can be any custom made or commercially available processor, a central processing unit (CPU), an auxiliary processor among several processors associated with the laptop 14B, a semiconductor based microprocessor (in the form of a microchip or chip set), a macroprocessor, or generally any device for executing software instructions.

The memory of the laptop 14B can include any one or combination of volatile memory elements (e.g., random access memory (RAM, such as DRAM, SRAM, SDRAM, etc.) and nonvolatile memory elements (e.g., ROM, hard drive, Flash, EPROM, EEPROM, CDROM, etc.). Moreover, the memory may incorporate electronic, magnetic, optical, semi-conductive, and/or other types of storage media. Note that the memory can have a distributed architecture, where various components are situated remote from one another, but can be accessed by the processor.

The software in memory of the laptop 14B may include one or more separate programs, such as interface software (e.g., middleware, such as browser software with or associated with one or more APIs) to communicate with other network devices, such as one or more computing devices 18, the separate programs each comprising an ordered listing of executable instructions for implementing logical functions. The software in the memory also includes application software and a suitable operating system (O/S). The operating system may be embodied as a Windows operating system available from Microsoft Corporation, a Macintosh operating system available from Apple Computer, a UNIX operating system, among others. The operating system essentially controls the execution of other computer programs, and provides scheduling, input-output control, file and data management, memory management, and communication control and related services. In some embodiments, application software stored in the memory may be used to provide processing functionality for one or more of the devices of the environment 10. For instance, processing to determine which wrist is associated with the wrist-worn device 12 and/or which hand is carrying the smartphone 14A may be offloaded (e.g., due to processing, power constraints) by the respective devices 12, 14A onto the laptop 14B, with the results communicated back to the devices 12, 14A. As indicated above, the laptop 14B may be coupled to a gaming apparatus and uses software similar to that described for the wrist-worn device 12 to determine to which limb the gaming apparatus is associated.

The I/O devices of the laptop 14B may include input devices, for example but not limited to, a keyboard, mouse, scanner, microphone, gaming apparatus, etc. Furthermore, the I/O devices may also include output devices, for example but not limited to, a printer, display, etc. For instance, the I/O devices embodied as a display screen may be used to present feedback and/or prompts to the user. The display screen of the laptop 14B may be configured according to any one of a variety of technologies, including cathode ray tube (CRT), liquid crystal display (LCD), plasma, haptic, among others well-known to those having ordinary skill in the art. In some embodiments, the I/O devices of the laptop 14B may including gaming devices, as described above, where the laptop 14B comprises application software to determine which hand or limb the gaming apparatus or control is attached to or held by.

When the laptop 14B is in operation, the processor is configured to execute the software stored within the memory, to communicate data to and from the memory, and to generally control operations of the laptop 14B pursuant to the software. Software can be stored on any non-transitory computer readable medium for use by or in connection with any computer related system or method. In the context of this document, a computer readable medium comprises an electronic, magnetic, optical, electromagnetic, infrared, or semiconductor system, apparatus, device or means that can contain or store a computer program for use by or in connection with a computer related system or method. The software can be embodied in any non-transitory computer-readable medium for use by or in connection with an instruction execution system, apparatus, or device, such as a computer-based system, processor-containing system, or other system that can fetch the instructions from the instruction execution system, apparatus, or device and execute the instructions.

The network 16 may comprise one or a combination of networks that enable communication between the wrist worn device 12, electronics devices 14, and the one or more computing devices 18. For instance, the network 16 may include a cellular network that includes the necessary infrastructure to enable cellular communications. There are a number of different digital cellular technologies suitable for use in the cellular network, including: GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others. As another example, the network 16 may include in addition to, or in lieu of the cellular network, an infrastructure to enable communications via one or a combination of other wired or wireless technologies, including Public Switched Telephone Networks (PSTN), Plain Old Telephone Service (POTS), Integrated Services Digital Network (ISDN), Ethernet, Fiber, Hybrid-fiber Coaxial (HFC), Digital Subscriber Line/Asymmetric Digital Subscriber Line (DSL/ADSL), Wireless-Fidelity/802.11 Zigbee, Bluetooth (BT), BT Low Energy (BTLE), among others.

The remote computing devices 18 of the PERS facility 20 may include one or more computing devices networked together, including an application server(s) and data storage. The PERS facility 20 may serve as a cloud computing environment (or other server network) for the wrist-worn device 12 and/or the electronics devices 14. In one embodiment, the PERS facility 20 serves as a call or PERS service center, receiving alerts or, in general, communications from the wrist-worn device 12 and/or the electronics devices 14 and providing service agents to communicate with the users of wrist-worn device 12 and/or the electronics devices 14 to assist in his or her emergency. In some embodiments, alerts may be used to trigger device action at the PERS facility 20 and/or elsewhere, including auto-dialing (e.g., to communicate with PERS agents, emergency personnel or family members), remote door unlock (e.g., signals to the user's residence to unlock the door for emergency personnel), remote light activation (e.g., activating an outdoor front light on and off to assist emergency personnel in finding the residence where the user is having an issue), among other device actions. Note that in some embodiments, the wrist-worn device 12 and/or the electronics devices 14 may communicate an alert (e.g., formatted as a text message or voice message or email) to other devices of individuals or entities that are designated (e.g., by the user) as recipients of the alert (i.e., that will assist the subject in the case of a fall or other emergency).

In some embodiments, such as for health, coaching, and/or gaming applications, the remote computing devices 18 may serve as a cloud computing environment (or other server network) for the wrist-worn device 12 and/or the electronics devices 14, performing processing and/or data storage on behalf of (or in some embodiments, in addition to) the wrist-worn device 12 and/or the electronics devices 14. When implemented in conjunction with a cloud platform, the remote computing devices 18 may be part of an internal cloud, an external cloud, a private cloud, or a public cloud (e.g., commercial cloud). For instance, a private cloud may be implemented using a variety of cloud systems including, for example, *Eucalyptus* Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, services of the remote computing devices 18 may be implemented according to multiple, logically-grouped servers (run on server devices), referred to as a server farm. The devices of the server farm may be geographically dispersed, administered as a single entity, or distributed among a plurality of server farms, executing one or more applications on behalf of or in conjunction with one or more of the wrist-worn device 12 and/or the electronics devices 14. The devices within each server farm may be heterogeneous. One or more of the devices of the server farm may operate according to one type of operating system platform (e.g., WINDOWS NT, manufactured by Microsoft Corp. of Redmond, Wash.), while one or more of the other devices may operate according to another type of operating system platform (e.g., Unix or Linux). The group of devices of the server farm may be logically grouped as a farm that may be interconnected using a wide-area network (WAN) connection or medium-area network (MAN) connection, and each device may each be referred to as (and operate according to) a file server device, application server device, web server device, proxy server device, or gateway server device.

Figure 2:
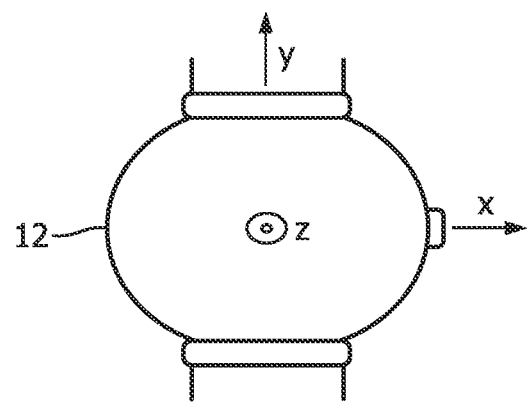
FIG. 2 is a schematic diagram that illustrates a right-hand coordinate system for a wrist-worn device, in accordance with an embodiment of the invention.

Having described various components of the example environment 10, attention is directed to FIG. 2, which illustrates a right-hand coordinate system for the wrist-worn device 12. In general, the 3D axes of an accelerometer are typically of a right-hand or left-hand 3D coordinate system (e.g., when curling index finger in an arc between the x- and y-axis, the direction of the thumb indicates the positive z-axis for left hand and right hand), with the right hand coordinate system being more common. These coordinate systems present conventions or rules for how the x-, y-, and z-axes are oriented relative to one another. For instance, in a standard configuration with the z-axis extending upwards and the x- and y-axes in the same plane, in a left hand 3D coordinate system the x-axis extends right, and in a right hand 3D coordinate system, the y-axis extends right. The accelerometer coordinate system is also aligned in a certain way relative to the wrist-worn device 12, and a typical example is shown in FIG. 2 for the right-hand coordinate system. Note that the x-axis is parallel to the watchcrown, the y-axis extends upward parallel to the strap of band of the wrist-worn device 12, and the positive z-axis extends out of the display (e.g., out of the page).

Figure 3:
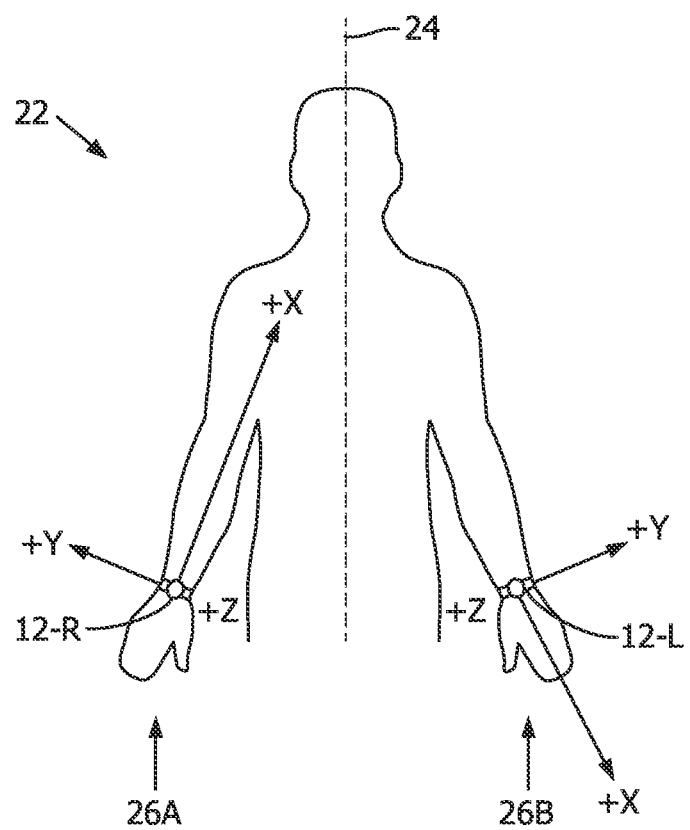
FIG. 3 is a schematic diagram that illustrates asymmetry in one axis when wearing the same wrist-worn device on the left or right wrist, in accordance with an embodiment of the invention.

Referring to FIG. 3, shown is a schematic diagram that illustrates asymmetry in one axis when wearing the same wrist-worn device 12, positioned in the same way, on the left or right wrist. In particular, a representation 22 of a user is shown facing forward, with a centerline 24 (shown in dashed line) dividing the representation 22 along a mid-sagittal plane, and a depiction of the wrist-worn device 12-R shown on the user's right wrist and a depiction of the wrist-worn device 12-L shown on the user's left wrist. Also superimposed on the user representation 22 are acceleration coordinate systems 26A for the wrist-worn device 12-R on the user's right wrist and acceleration coordinate system 26B for the wrist-worn device 12-L on the user's left wrist. Taking this example of the wrist-worn device 12 worn on the user's left (wrist-worn device 12-L) and right (wrist-worn device 12-R), it is observed that a symmetry exists for both the y- and z-axis, but that the x-axis displays anti-symmetry for the two wearing locations. In other words, when standing, the positive x-axis points downwards when wearing the wrist-worn device 12-L on the left wrist, while upwards along the arm axis when wearing the wrist-worn device 12-R on the right wrist. Certain embodiments of a wrist-worn device exploit this asymmetry along the x-axis to determine whether the device is being worn on the left or right wrist. Note that in some embodiments, a left hand coordinate system may be used and/or a different axis may be exploited, including signal projections onto a new 3D space (e.g., eigen-projections). This may affect the signs of the observed signals. Also, axes may be oriented in different manner than as depicted. For instance, the y-axis may be oriented along the arm direction in some embodiments as expressed above. It may also happen that the physical axes are not aligned/along the body axes, and a rotation or alike operation is applied to obtain signals as if they were aligned.

Figure 4A:
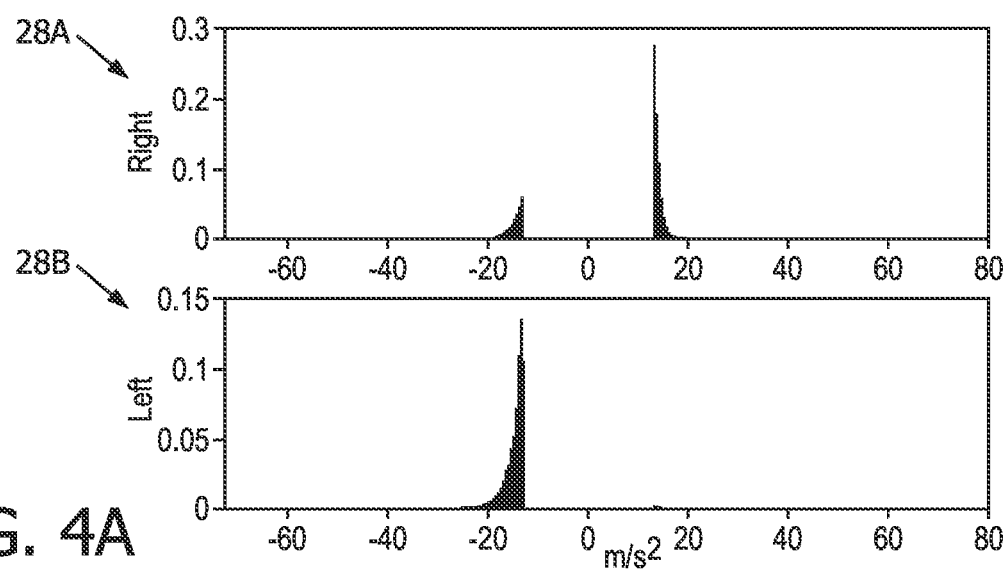
FIGS. 4A-4C are plot diagrams that illustrate distributions of x, y, and z-axis accelerometer signals for a wrist-worn device worn on the left (bottom plots) and right (top plots) wrists, in accordance with an embodiment of the invention.
Figure 4B:
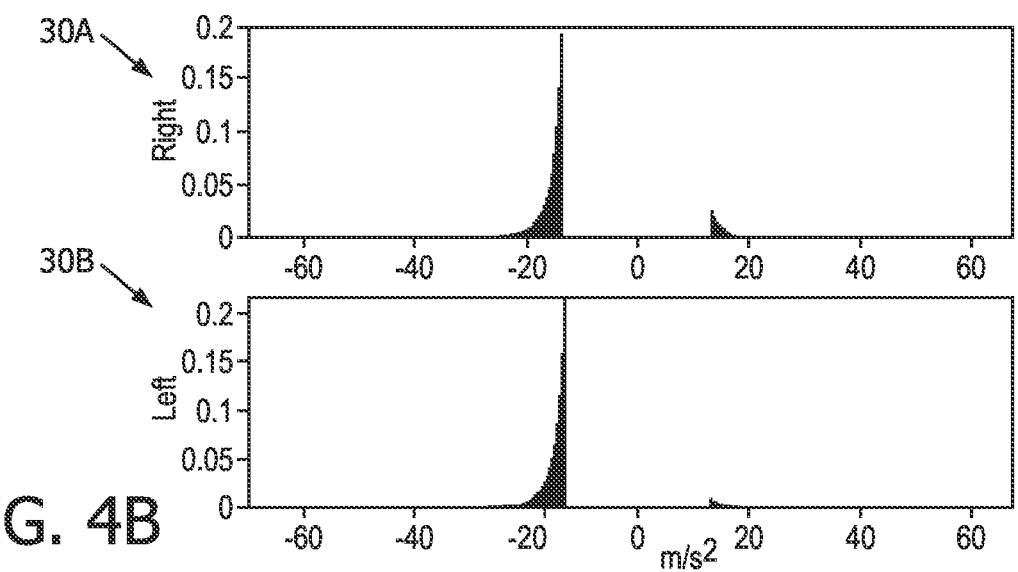
Figure 4C:
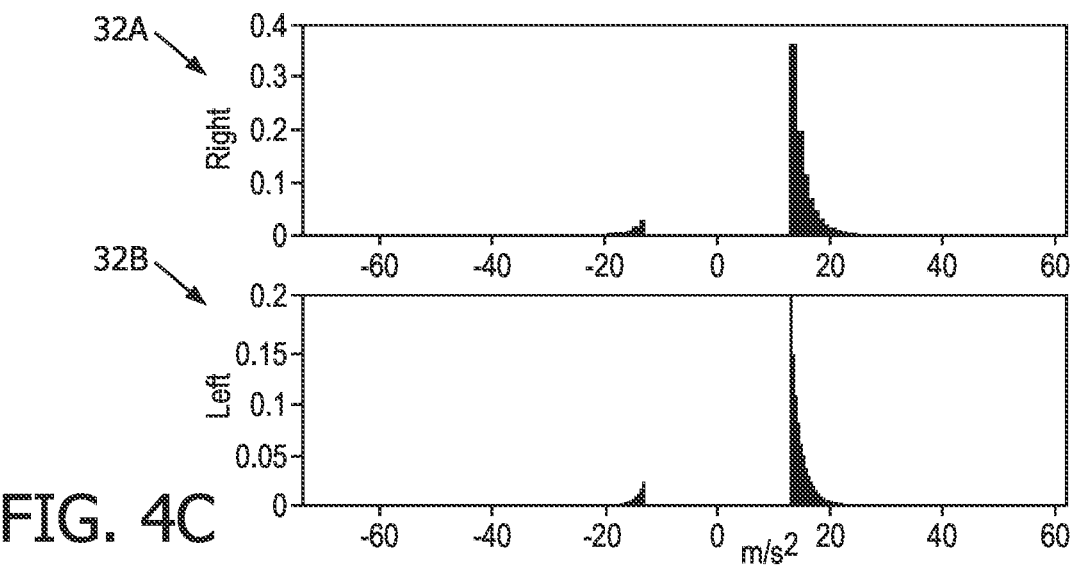

FIGS. 4A-4C are plot diagrams that illustrate distributions of x, y, and z-axis accelerometer signals for a wrist-worn device worn on the left and right wrists. All the plots depicted in FIGS. 4A-4C use a threshold of 13 m/sec2, though in some embodiments, other values may be used based, for instance, on the specified margin (as explained below). In some embodiments, other units may be used, such as an integer value as provided by the sensor device. For instance, the threshold may be scaled accord to the equivalent value in that unit. Some devices may provide set threshold(s) within the chip. Referring to plot diagram 28A, shown is a right wrist, x-axis accelerometer value distribution. Plot diagram 30B is a left wrist, x-axis accelerometer value distribution. Plot diagram 30A is a right wrist, y-axis accelerometer value distribution. Plot diagram 28B is a left wrist, y-axis accelerometer value distribution. Plot diagram 32A is a right wrist, z-axis accelerometer value distribution. Plot diagram 32B is a left wrist, z-axis accelerometer value distribution. What may be observed from these plot diagrams 28-32 is that the distribution tails of acceleration values for the x-, y-, and z-axes of a wrist-worn device 12 follow the accelerometer coordinate system convention shown in FIGS. 2-3 for a user wearing the wrist-worn device 12 throughout the day. For these plot diagrams 28-32, the remainder of the distributions around their mean have been excluded for clarity. Note that the tails of these distributions are more pronounced and biased in a certain direction (positive/negative) depending on the wearing location. As explained further below, it is through filtering of samples according to one or more thresholds that the distribution tails may be isolated.

In fact, this bias may be attributed to acceleration components superimposed on the gravitational norm vector. The gravitational norm vector has a magnitude equal to the gravitational acceleration, 9.81 m/s$^2$, but in the opposite direction to the gravity. For an accelerometer at rest or in motion with a constant velocity, this component is present and due to the design of accelerometer sensors, which can be seen as a spring mass system. When a user is wearing the wrist-worn device 12 (and thus wearing the accelerometer) on the wrist such as depicted in FIGS. 2-3, the gravitational norm is either near or along the positive or negative x-axis. When a person walks, the normal force of the surface imparted to the body, therefore, either reinforces the gravitational norm vector along the positive or negative x-axis. Note the asymmetry in the x-axis signals between the two wearing locations versus no asymmetry for y- and z-axes. For other hand movements, or postures and gestures, the gravitational vector is more randomly distributed among the other sensor axes.

Figure 5A:
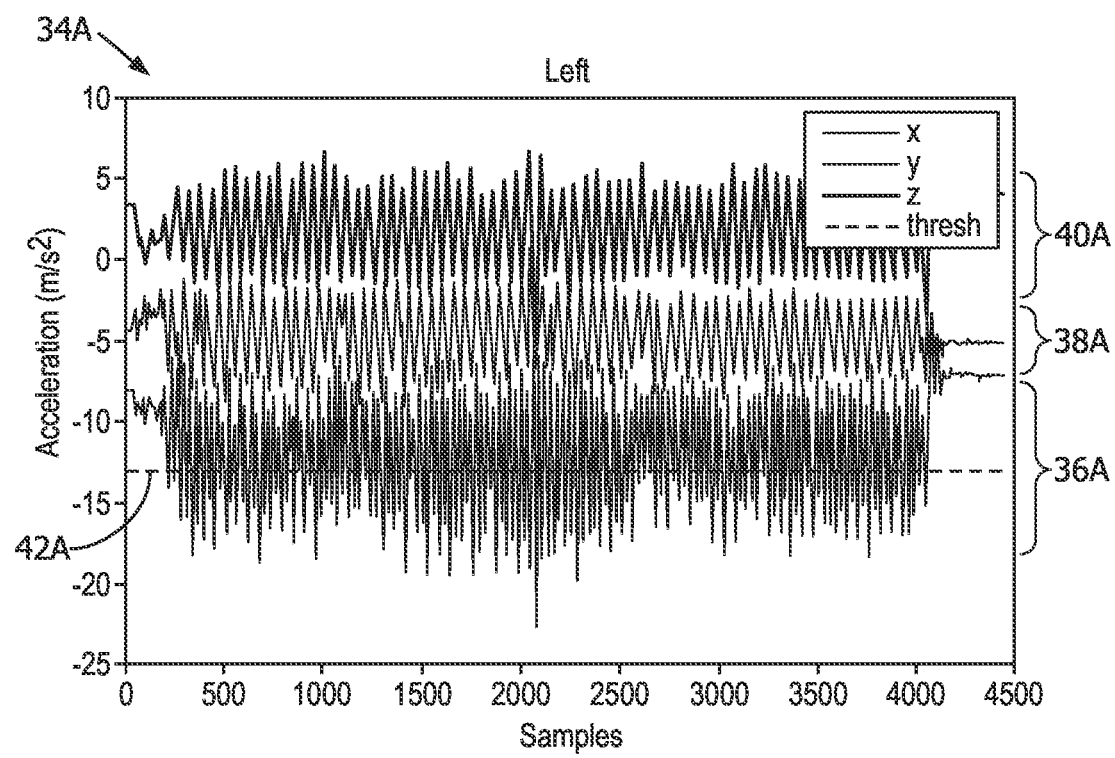
FIGS. 5A-5B are plot diagrams that illustrate example accelerometer signals during walking for left and right wrist placement of a wrist-worn device during walking, in accordance with an embodiment of the invention.
Figure 5B:
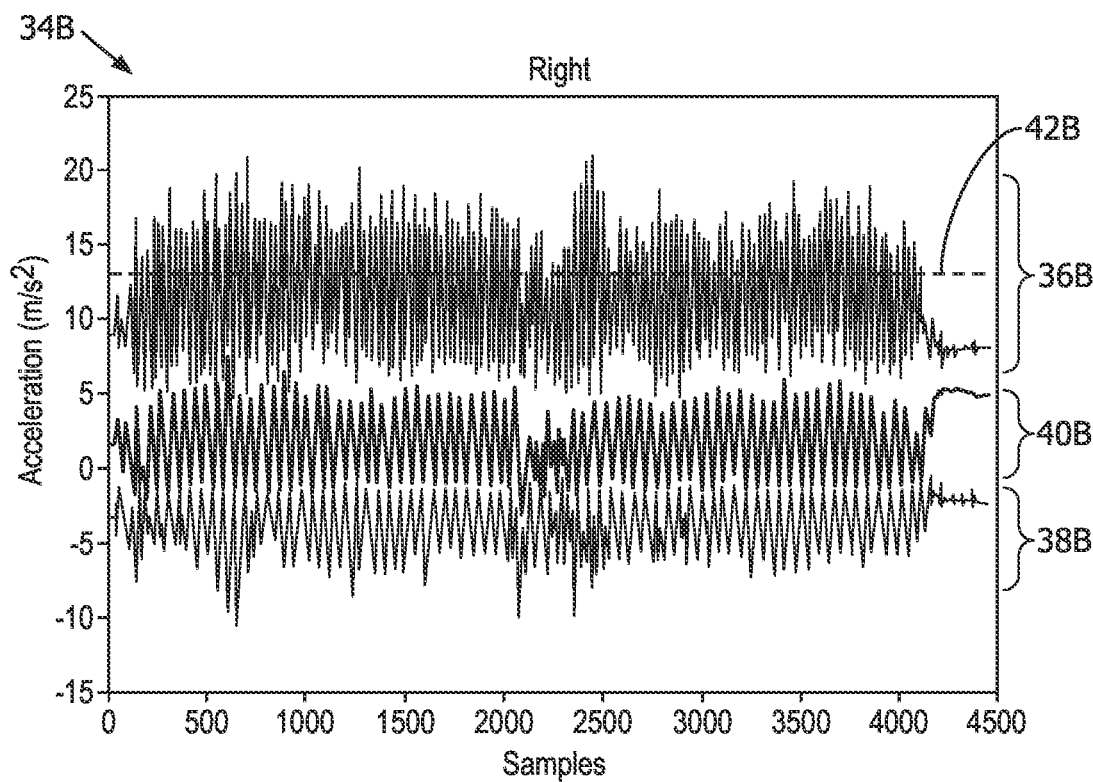

FIGS. 5A-5B are plot diagrams that illustrate example accelerometer signals for left and right wrist placement of a wrist-worn device 12 during walking. Plot diagram 34A of FIG. 5A shows accelerometer values for the left wrist placement as a function of the number of samples, and plot diagram 34B shows accelerometer values for the right wrist placement as a function of the number of samples. Though a legend is depicted in the upper right hand side of the plot diagrams 34A, 34B, accelerometer values are similarly denoted as x-axis accelerometer values 36A, 36B (36A for the left wrist or plot diagram 34A, 36B for the right wrist of plot diagram 34B), y-axis accelerometer values 38A, 38B (38A for the left wrist or plot diagram 34A, 38B for the right wrist of plot diagram 34B), and z-axis accelerometer values 40A, 40B (40A for the left wrist or plot diagram 34A, 40B for the right wrist of plot diagram 34B). Simply by accumulating these acceleration values over time, functionality of the wrist worn device 12 can determine whether the watch is being worn on the left wrist or right wrist. In one embodiment, only values having a magnitude that falls outside of a predefined (or in some embodiments, learned) range determined by a threshold above 9.81 m/s$^2$ are accumulated. This function may be viewed as a pre-filtering step. Referring to FIG. 5B and focusing on the x-axis accelerometer values 36 (since this axis based on the accelerometer coordinate axis reveals asymmetry between left and right wrist placement), if the accumulated accelerometer values are greater than a specific threshold 42B (shown as having a value of +13 m/sec$^2$ as an illustrative, non-limiting example), as indicated by the x-axis accelerometer values 36B, then this indicates that the wrist-worn device 12 is being worn on the right wrist, while an accumulated value of less than another specified threshold 42A (shown as having a value of −13 m/sec$^2$ as an illustrative, non-limiting example), as indicated by the x-axis accelerometer values 36A, then this indicates that the wrist worn device 12 is worn on the left wrist. Note that while surface impacts with feet also influence the other axes, the gravitational component is strongest and is modulated by these impacts.

Figure 6:
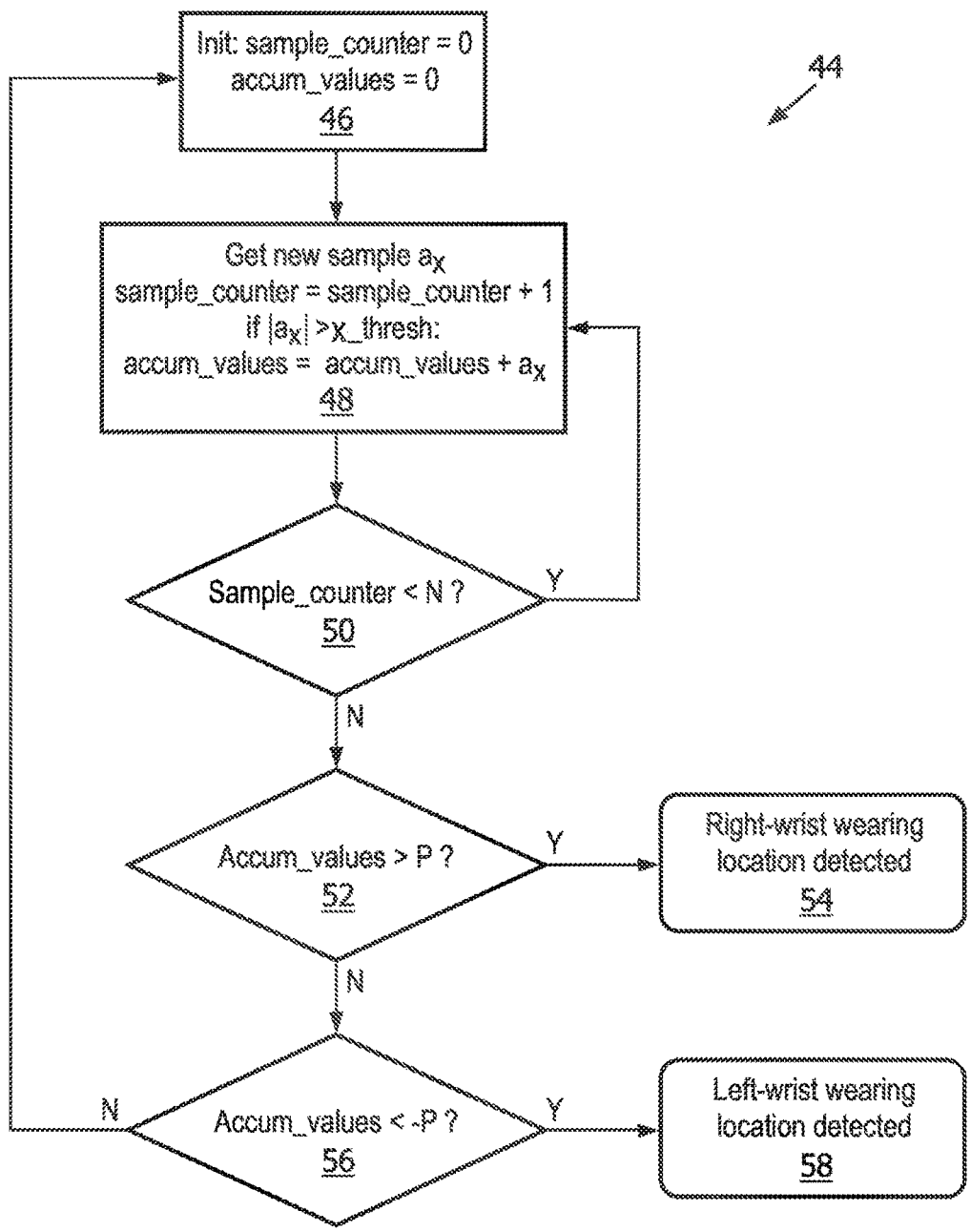
FIG. 6 is a flow diagram that illustrates an example wrist placement determination method for a wrist-worn device, in accordance with an embodiment of the invention.

Attention is now directed to FIG. 6, which is a flow diagram that illustrates an example wrist placement determination method 44 for an embodiment of a wrist-worn device 12. In one embodiment, the method 44 may be implemented by the wrist-worn device 12. In some embodiments, the method 44 may be implemented in another device (e.g., electronic device 14, remote computing device 18), or the method may be implemented in some embodiments by plural devices (e.g., in a client-server relationship or distributed computing environment, or where the accelerometer is located externally or remote from the device). It should be appreciated by one having ordinary skill in the art, in the context of the present disclosure, that steps depicted in the method 44 of FIG. 6 may be re-ordered, or that additional or fewer steps may be used in some embodiments. As is described further below, the method 44 may generally be viewed as an algorithm that accumulates filtered acceleration values from the distribution tails over time and determines whether the wrist-worn device 12 (e.g., watch) is being worn on the left or right wrist. In one embodiment, if the total accumulated value is greater than a certain threshold, then this indicates that the device is being worn on the right wrist, while an accumulated value of less than a second (negative) threshold indicates that the device is worn on the left wrist. Note that the aforementioned first and second, signed thresholds may also be referred to as a threshold set. In some embodiments, the threshold set may be achieved using a single threshold value plus a sign component. This tail-threshold approach is beneficial since it does not require the explicit detection of walking, which is known to be indicative of wearing location.

Before describing the method 44, a brief description of parameters used in the method 44 is provided below. At least three parameters are referenced in the method 44, including N, P, and x_thresh. N refers to an observation window over which an estimate about left/right wrist wearing location is made, P refers to an accumulation threshold above which a decision about wearing location is made, and x_thresh refers to a threshold (a filtering threshold, resulting in filtered accumulated samples) used to accumulate tail acceleration values. These three parameters are implicitly related since, for instance, setting a low value of x_thresh may result in more data points being accumulated in the distribution tails, meaning that P should be increased to preserve accuracy. Similarly, increasing N should be accompanied by an increasing P since more samples from the distribution tails are collected. Further description of these parameters and example values for them are described below.

Referring now to method 44, sample counter and (acceleration) value-accumulation variables are initialized to zero (46). The sample counter (sample_count) counts the number of (filtered) accelerometer samples used to calculate the given accumulation of values, accum_values. In (48), a sample $a_x$ is acquired, the sample count is incremented, and an absolute value of the sample $a_x$ (having a sub-value) is checked against a first pre-defined threshold, x_thresh. This thresholding can be seen as a pre-filtering step, and is used to isolate only those samples in the tail of the distribution, which are accumulated (as filtered accumulated samples) in the variable accum_values (which comprises the accumulation of sub-values). In some embodiments, the accum_values may include normalized values, as explained below. The accum_values also accounts for the sign of each of the sub-valued samples. One advantage of such a first threshold is that sample values attributed to non-related activities are excluded from the estimation procedure. In (50), if the sample count is less than a pre-defined value of N (sample_counter<N), then (Yes) a new sample is acquired (48).

After N samples have been analyzed (No in (50)), the value of accum_values is compared against a threshold P (52). In effect, the accum_values comprises a simple summation of sub-samples with a respective absolute value ($|a_x|$) (sub-value) above a certain threshold, x_thresh, where in (52)-(54), the accum_values is tested against + or −P (e.g., one embodiment of a threshold set). For this method embodiment, N and P are used to collect and test the evidence, to prevent false detections. It could be that the user was engaged in a short activity that led to extreme tail values, but was not consistent enough to actually indicate wearing location. These could include certain impacts with the wrist, etc. If the value of accum_values is greater than P (Yes to (52)), then the wrist-worn device 12 is estimated as worn on the right wrist of the user (54). If the value of accum_values is not greater than P (No to (52)), then a determination is made as to another threshold (56), or rather, is accum_values<−P. If the value of accum_values is less than −P (Yes to (56)), then the wrist-worn device 12 is estimated as worn on the left wrist of the user (58), otherwise processing returns to (46).

Explaining the parameters further, the observation window N should be long enough to capture sufficient information about the acceleration distribution tails, but short enough to reduce the time required to produce a wearing location estimate. In one embodiment, setting N between 3 and 10 minutes (typically 5 minutes) is sufficient to capture this information, though in some embodiments, other values or range of values may be used depending on the specifications of the wrist-worn device 12 or application (e.g., when used for determining which hand is carrying the device or which lower limb the device is strapped to) or user health condition/activity level. In some embodiments, an observation window may be omitted and the wearing location is tested in contiguous sample batches of length N. In some embodiments, N may be adapted in the case of several iterations/results of "No" in the determination in (56) and, optionally, if the accumulated sum of $|a_x|$ is greater than a given value (e.g., a value indicative of movement). For continuous monitoring and detection, the value of accum_values can be continuously updated. Once accum_values is greater than P or less than −P, a wearing location decision is made, and the value of accum_values reset.

In one embodiment, the value of P may be set to 400 m/s$^2$, and may be increased further to reduce the number of false detections. In some embodiments, other values or range of values may be used.

Note that variations to the method 44 are also contemplated to provide further refinement in the determination of which wrist the wrist-worn device 12 is placed. In one embodiment, a magnitude of x_thresh in (48) of the method 44 should be set above the gravitational norm magnitude of g=9.81 m/s$^2$ by a certain margin Δx. A value of the margin Δx of approximately 3-4 m/s$^2$ is sufficient to capture the relevant samples in the tail of the acceleration distribution, though other values or range of values may be used in some embodiments.

It may also be appreciated that the determination of the above margin Δx is predicated on the assumption that the accelerometer is calibrated. In other words, a stationary sensor should exhibit the gravitational norm vector accurately when placed horizontally on one of its axes. Typically, accelerometers can exhibit some biases on one or more of their axes (e.g., may not perfectly reproduce the gravitational norm values when at rest due to scaling/offset biases), which may have implications for thresholding (e.g., different thresholds in +/−direction). Calibration is described further below.

Further, accelerometers typically exhibit a specific dynamic range, r, often presented in terms of the gravitational force g (e.g., +/−2 g, 4 g, 8 g, 16 g). In one embodiment, the accumulated acceleration values $a_x$ in (48) of the method 44 are first normalized (or in some embodiments, use the (integer) units provided by the sensor as explained above) by the dynamic range before accumulation according to the following equation:

$$\text{accum\_values} = \text{accum\_values} + a_x/r \qquad \text{(Eqn. 1)}$$

Implementation of Eqn. 1 serves more as a normalization of the acceleration data to lie between −1.0 and 1.0. The dynamic range may be linked to the type of accelerometer (e.g., is manufacturer dependent), but in some instances, may also be a setting of a given accelerometer. Typically, most MEMS accelerometers nowadays can be operated in different modes corresponding to different dynamic ranges, depending on what the user requires.

In some embodiments, the condition at (48) of the method 44, namely, if $|a_x|$>x_thresh, may be modified to also include an upper bound (e.g., threshold) on the acceleration to isolate common human activity patterns and movements, excluding spurious wrist impacts, according to the following equation:

$$\text{if } |a_x| > \text{x\_thresh\_low and } |a_x| < \text{x\_thresh\_high}, \qquad \text{(Eqn. 2)}$$

where the value of x_thresh_high may be set to 20 m/s$^2$ in one embodiment, though not limited to this value (e.g., in some embodiments, other upper thresholds may be used).

In some embodiments, the values for various thresholds and observation windows may be selected based on distributions estimated within a training period, during which the user wears the wrist-worn device 12 on both wrists for a certain period, such as a few days. That is, in one embodiment, distributions are estimated from each wrist from an existing target user, since the data distributions will vary depending on factors such as mobility. The selection of values of these parameters may represent a trade-off in accuracy and trigger rate (e.g., sensitivity). In some embodiments, one or more of the parameters and/or thresholds may be tuned for specific class of users. For instance, some users make use of walking aids, including walkers, canes and wheelchairs. Using mobility aids changes the direction of the wrist during walking and may result in lower trigger rates for the detection algorithm, leading to delays in correctly estimating the wearing location. The algorithm parameters N, P, and x_thresh may be tuned for this specific class of users, particularly those that make permanent use of such walking aids.

In some embodiments, using machine learning or statistical methods (e.g., using quartiles), the average of the left and right distribution tails may be calculated, and the absolute difference in the average values may then be calculated to set a value for P. It is noted that use of statistical methods (e.g., a priori or during a training phase) may result in a different set of thresholds in the +/−directions for x_thresh and/or P if sensors are not calibrated. For example, the x-axis may be biased in the positive direction (e.g., the x_thresh(+) may be larger than x_thresh(−)). In practice, these biases are usually minor for accelerometers.

In some embodiments, the value accum_values is only updated during periods of activity. Activity detection may be performed based on the average standard deviation of the three accelerometer axes, or simply based on the standard deviation of the x-axis signal.

In some embodiments, compliance detection supplants the activity detection by detecting that the device is actually being worn. This may be achieved using proximity or capacitive sensors (e.g., of the wrist-worn device 12), which cause a change in signal characteristic based on whether the wrist-worn device 12 is worn close to the skin or not. Note that the use of the counter N and the set of thresholds (+/−P) also bolster the robustness of the wrist placement determination process.

In the foregoing description, the x-axis acceleration samples values each with a magnitude (sub-value) that exceeds a tail-distribution threshold x_thresh are accumulated to obtain a subset of samples that can be used to detect left-right wearing locations. In some embodiments, such filtering may not be based on magnitude (e.g., when using plural thresholds or a threshold with a sign component). This detection measure is an accumulation of the tail acceleration (sub) values. When most of these values are positive and along the same direction as the gravitational norm vector, enough acceleration is measured so that in one embodiment the total sum can exceed a threshold P (or falls below −P) to make a decision on the wearing location. To minimize any risk of false detections in the event of numerous impacts or acceleration spikes along the x-direction (which can lead to erroneously large values of accum_values in the wrong direction), some embodiments of a wrist worn device 12 use an algorithm that replaces accum_values with two variables, count_tailL and count_tailR, which hold the number of acceleration samples in the two tails of the distribution of x-axis acceleration samples. A ratio measure, denoted by Eqn. 3 below, may then be used to determine whether the device is worn on the left or right wrist:

$$W_{LR} = \frac{\text{count\_tailR} - \text{count\_tailL}}{\text{count\_tailR} + \text{count\_tailL}}, \quad \text{Eqn. 3}$$

$$W_{LR} \in [-1, 1]$$

where count_tailR and count_tailL are incremented by one if the value of $a_x > \text{x\_thresh}$ and $a_x < -\text{x\_thresh}$, respectively. The bounded values of WLR may then be compared to a threshold similar to P, denoted by PLR here, with the test for wearing location according to the following set of thresholds:

$$\text{Wearing location} = \begin{cases} \text{Left wrist if } W_{LR} < -P_{LR} \\ \text{Right wrist if } W_{LR} > P_{LR} \\ \text{Undetermined if } |W_{LR}| \le P_{LR} \end{cases}$$

In one embodiment, a typical value of PLR is 0.2, though other values may be used in some embodiments. If a detection is made (left or right wrist), both counters count_tailR and count_tailL are reset.

Although certain embodiments of a wrist-worn device obviate the need for extensive data collection, in some embodiments where sufficient resources (e.g., in terms of processing power and memory) are available, historical data may be helpful. For instance, a histogram may be used in some embodiments to determine x_thresh adaptively, where the threshold may be set as a percentage of data points lying outside the range +/−x_thresh. However, in such an embodiment, designers need to be mindful that while accuracy may improve for higher thresholds (smaller percentage of tail samples), the resulting trigger rate may decrease, and thus may lead to distribution-dependent delays in wearing location detection. Keeping this delay low is particularly important for users who often switch the wearing location of their device.

Figure 7A:
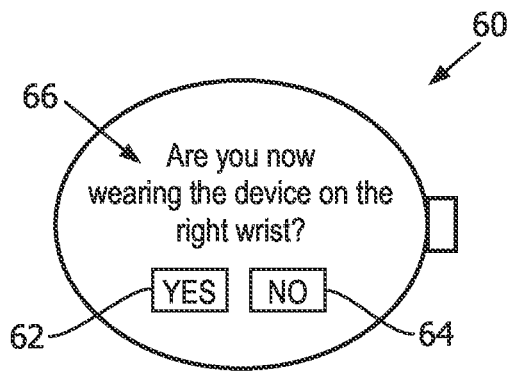
FIG. 7A is a schematic diagram that illustrates an example user interface with a prompt that asks a user to confirm a newly detected wearing location, in accordance with an embodiment of the invention.

Referring now to FIG. 7A, shown is a schematic diagram that illustrates an example user interface 60 with a prompt that asks a user to confirm a newly detected wearing location. For instance, once a determination is made of the wearing location according to the method 44 of FIG. 6, in some embodiments, the wrist-worn device output (e.g., wrist-worn device placement 54 or 58) corresponding to the detection/determination result may be used to prompt the user for a confirmation of the wearing location. In effect, the prompt is presented to confirm a wearing location in case a different location is detected by the algorithm. In this case, the smartwatch's wearing location setting was set to left, but the algorithm detects that the user is wearing the device on the right wrist. The user interface 60 may be integrated in the wrist-worn device 12, though in some embodiments, may be presented on another device (e.g., electronics device 14). As shown, the user interface 60 comprises YES 62 and NO 64 icons (e.g., pertaining to adjacent switches or hard buttons) or labeled software buttons, and presents the question 66, "are you now wearing the device on the right wrist", or similar messaging as applicable. In some embodiments, other and/or additional presentation/prompt features may be used, including a different prompting mechanism (e.g., using LED lights or other graphics), different content (e.g., message), with differences still retaining the same the same or similar purpose for the prompt. In some embodiments, the prompt may be presented in association with an audible and/or tactile feature (e.g., beeping sound to alert of the prompt, buzzing sensation to alert of the prompt, etc.).

Figure 7B:
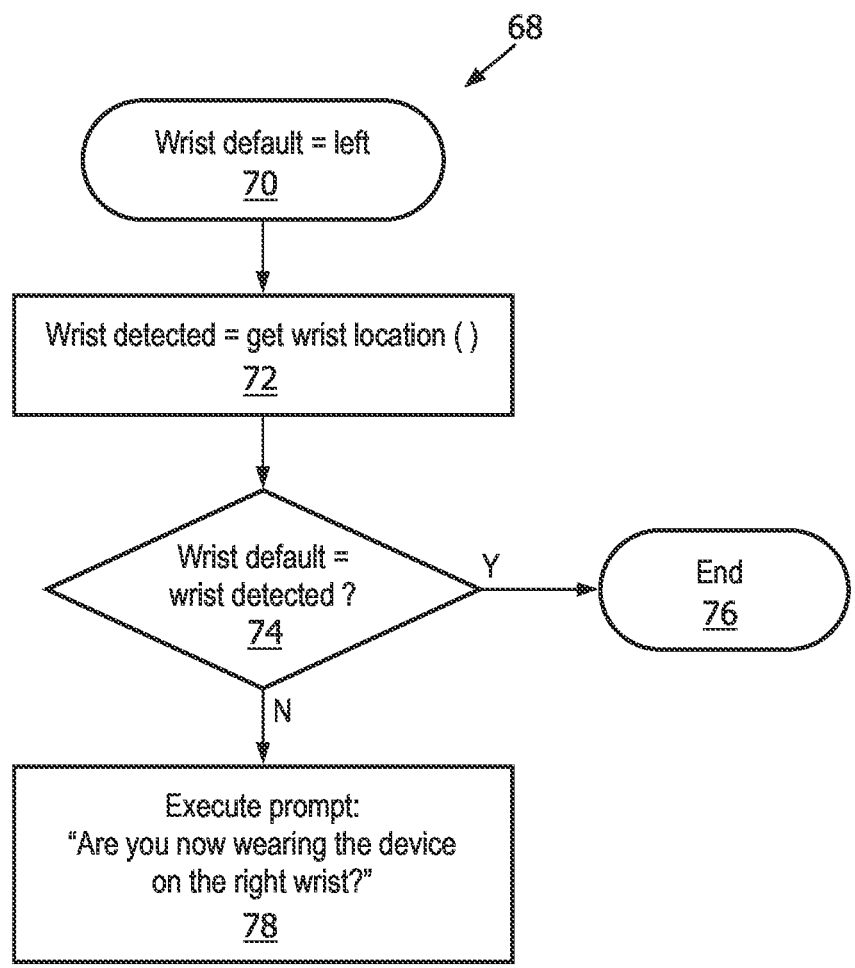
FIG. 7B is a flow diagram that illustrates an example method for providing the prompt of FIG. 7A, in accordance with an embodiment of the invention.

FIG. 7B is a flow diagram that illustrates an example method 68 for providing the prompt of FIG. 7A. As indicated above, the prompt may be presented at the wrist-worn device 12 or other or additional devices. In one embodiment, the method 68 comprises determining a wrist-location default (70). In the example shown in FIG. 7B, the default location is the left wrist for illustration. The default may be an initial wearing location, one that was set by the user (e.g., in a device settings menu), and/or the last determined wrist location. The method 68 further comprises invoking the results of the method 44 to determine the wrist location after detecting that the wrist-worn device 12 is on the user's wrist (72). The result of the method 44 determining which wrist the wrist-worn device 12 is placed on is used to prompt a test of whether the location is the same as the default location (74). If so (Yes), the method 68 terminates (76). If not (No), the method 68 provides the prompt (78) shown, as an example, in the user interface 60 of FIG. 7A. Once the wearing location has been confirmed and switched, this location is stored and used to test any newly detected location. To reduce the number of prompts, the values of N and P may be increased for every false detection, and otherwise decreased or reset to their initial values.

In the embodiments described above, emphasis is placed on reliance on a single accelerometer axis (e.g., the x-axis) for data used to support a determination of wrist placement for a wrist-worn device 12. However, in some embodiments, the wrist-worn device 12 may use an additional axis of the accelerometer (e.g., the y-axis) to determine how the wrist device is worn in situations where the watchcase is rotated (e.g., rotated 180 degrees with respect to the wrist), such as in a wrist-worn device 12 embodied as a smartwatch with a physical crown. That is, the watchcase may be rotated while wearing the wrist-worn device 12, and this event may corrupt or otherwise render wearing location determinations inaccurate. Some devices, in particular dedicated OEM watches, might be symmetric, lacking a preferred orientation. For some users, a protruding crown on the wrist-worn device 12 may lead to discomfort when worn on the left wrist. Typically, a watches crown is positioned at or near the 3 o'clock location of its dial. Owing to certain physiology, wearing such a watch on the left wrist may result in the crown impinging on the base of the left hand. For other left-wearing users, having a smartwatch's push crown at or near the 9 o'clock dial-location allows easier access for a thumb press.

Figure 8A:
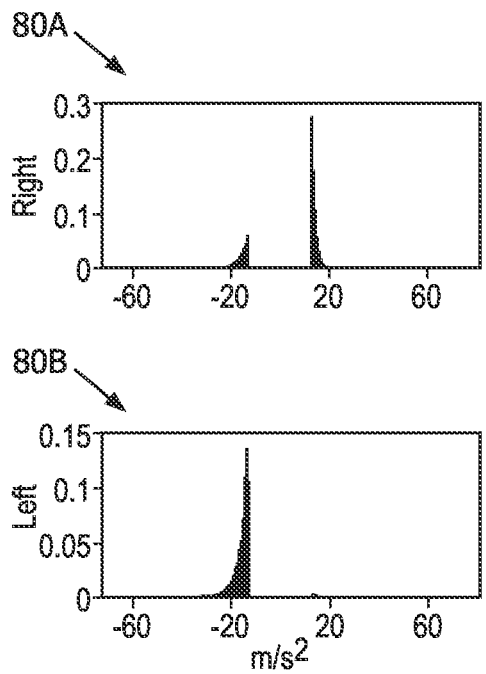
FIGS. 8A-8D are plot diagrams that provide an illustrative comparison of isolated distribution tails along the x and y axis with and without watchface rotation, in accordance with an embodiment of the invention.
Figure 8B:
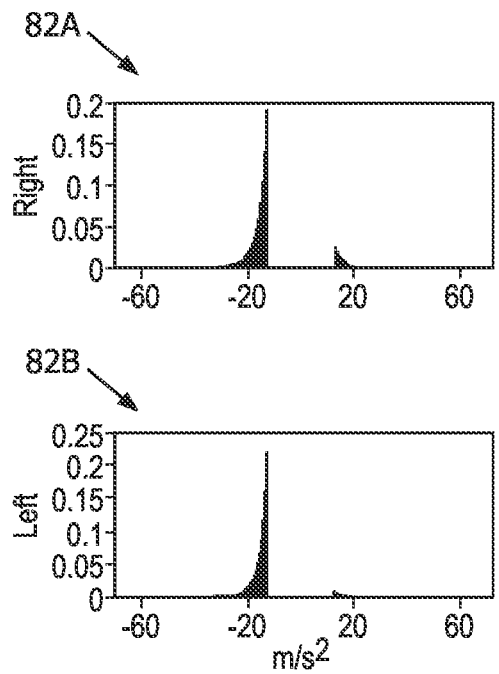
Figure 8C:
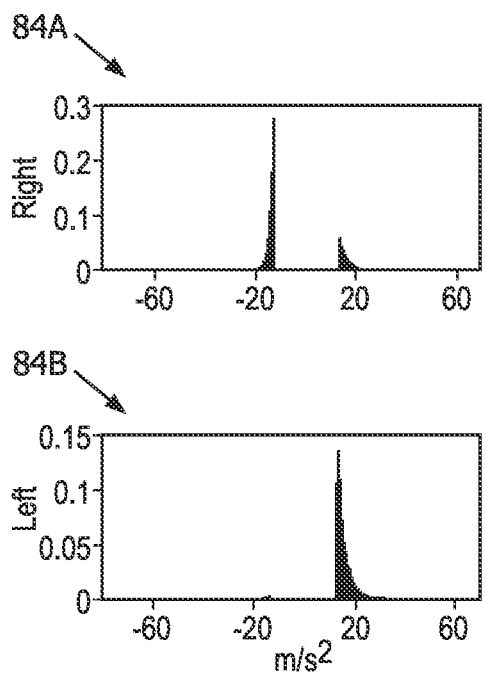
Figure 8D:
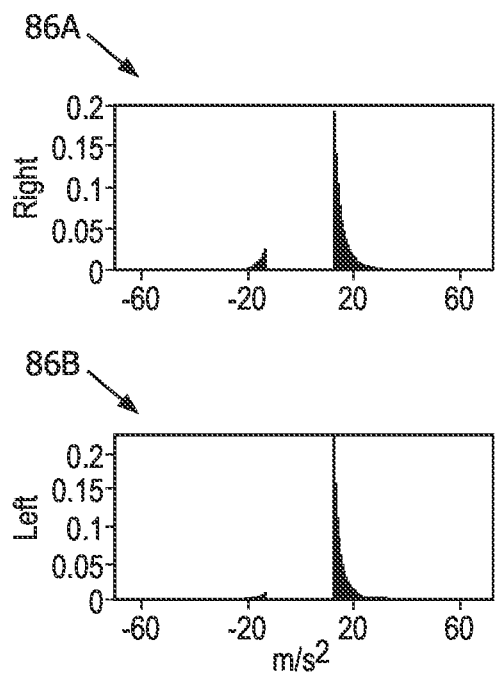

To understand how watchcase rotations may be detected, reference is made to FIGS. 8A-8D, which are plot diagrams that provide an illustrative comparison of isolated distribution tails along the x and y axis with and without watchface rotation. FIG. 8A comprises plot diagrams 80A, 80B for x-axis accelerometer (tail) distributions for a right-wrist placement (80A) and a left-wrist placement (80B) of a wrist-worn device. FIG. 8B comprises plot diagrams 82A, 82B for y-axis accelerometer (tail) distributions for a right-wrist placement (82A) and a left-wrist placement (82B) of a wrist-worn device. FIG. 8C comprises plot diagrams 84A, 84B for x-axis accelerometer (tail) distributions for a right-wrist placement (84A) and a left-wrist placement (84B) of a wrist-worn device. FIG. 8D comprises plot diagrams 86A, 86B for y-axis accelerometer (tail) distributions for a right-wrist placement (86A) and a left-wrist placement (86B) of a wrist-worn device. The x-thresh for each of the plots 80-86 is 13 m/sec$^2$, though in some embodiments, other values may be used. Comparing the left and right plots, it is observed that for the right wrist, the x- and y-axis tails are always largest in opposing acceleration direction, even if the wrist-worn device is rotated 180 degrees. For the left wrist, however, one notes that the largest tails occur in the same acceleration direction (negative-negative for standard and positive-positive for rotated).

From distributions such as those noted above (as illustrated in the plot diagrams 80-86 in FIGS. 8A-8D), one embodiment of a wrist-placement location algorithm is designed so that it includes the accelerometer's y-axis distribution tail information to determine the wrist wearing location, while being agnostic as to whether the device's case is also rotated. One approach is to build x- and y-axis distribution tails (or respective accum_value values) and compare their sign. If their signs are equal, then the wearing location is determined to be the left wrist, with the extra rotational information signaling the correct direction of the accelerometer's x-axis.

Figure 9:
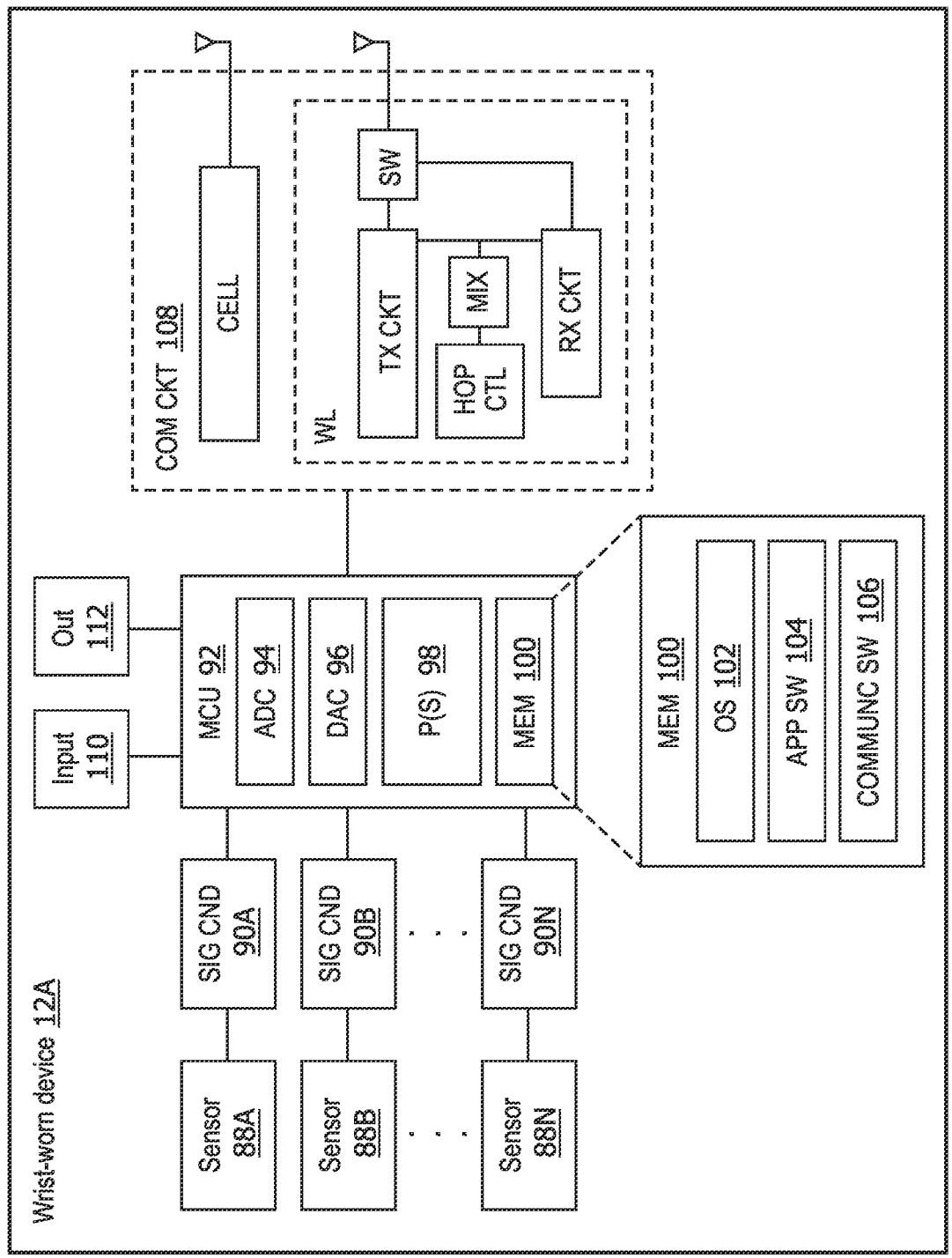
FIG. 9 is a block diagram that illustrates an example wrist-worn device configured to automatically determine left or right wrist placement of the wrist-worn device, in accordance with an embodiment of the invention.

Having described various functionality underlying certain embodiments of a wrist-worn device 12, attention is directed to FIG. 9, which illustrates an embodiment of an example wrist-worn device 12A configured to automatically determine left or right wrist placement. For instance, FIG. 9 illustrates example circuitry for the example wrist-worn device 12A, and in particular, underlying circuitry and software (e.g., architecture) of the wrist-worn device 12A. It should be appreciated by one having ordinary skill in the art in the context of the present disclosure that the architecture of the wrist-worn device 12A depicted in FIG. 9 is but one example, and that in some embodiments, additional, fewer, and/or different components may be used to achieve similar and/or additional functionality. In some embodiments, one or more of the functionality of the wrist-worn device 12A may reside in the electronics devices 14 or remote computing device 18, as described above. In one embodiment, the wrist-worn device 12A comprises one or more sensors, shown here with plural sensors 88 (e.g., 88A-88N), one or more signal conditioning circuits 90 (e.g., 90A-90N) coupled respectively to the sensors 88, and a microcontroller 92 that receives the conditioned signals from the signal conditioning circuits 90. In one embodiment, the microcontroller 92 comprises an analog-to-digital converter 94, a digital-to-analog converter 96, one or more processors 98, and memory 100. In some embodiments, the microcontroller 92 may comprise fewer or additional components than those depicted in FIG. 9, and in some embodiments, functionality of the microcontroller 92 may be performed by one or more other devices. The memory 100 comprises an operating system 102, application software 104, and communications software 106. The application software 104 comprises instructions/executable code to implement methods 44 (FIG. 6), 68 (FIG. 7B), and other methods/algorithms described above (e.g., left and right tail distribution counters, watchface rotation implementations, etc.). The communications software 106 cooperates with various communications hardware circuitry to enable the wrist-worn device 12A to operate according to one or more of a plurality of different communication technologies (e.g., GSM, WCDMA, 3G, 4G, 5G, NFC, Bluetooth (BT), BT low energy (BTLE), Wi-Fi/802.11, Zigbee, etc.). In some embodiments, the communications software 106 may be part of the application software 104 or located in separate or other memory.

The memory 100 further comprises one or more data structures that store, among other data, data (e.g., parameters, thresholds, etc.) recorded from a training period. In some embodiments, the data structures may be stored elsewhere and accessed from another device. In one embodiment, the microcontroller 92 is coupled to a communications circuit 108. The communications circuit 108 comprises hardware/software necessary to enable wireless and/or cellular communications between the wrist-worn device 12A and other devices, including electronics devices 14 and/or the computing devices 18 (via a cellular, wireless, and/or wired network connection). The communications circuit 108 is described below primarily (for illustrative, yet non-limiting purposes) as enabling the wrist-worn device 12A to communicate with the computing devices 18 via the electronics devices 14 as intermediate devices, with the understanding that the communications circuit 108 may include additional functionality to enable communications with the computing devices 18 without the use of the electronics devices 14 as an intermediary (e.g., via cellular hardware/software). The communications circuit 108 is depicted as comprising wireless functionality in the form of a Bluetooth circuit, though not limited to this transceiver configuration. For instance, in some embodiments, the communications circuit 108 may be embodied as any one or a combination of an NFC circuit, Wi-Fi circuit, Bluetooth Low Energy (LE)

circuit, transceiver circuitry based on Zigbee, among others such as optical or ultrasonic based technologies. The microcontroller 92 is further coupled to input/output (I/O) devices or peripherals, such as an input interface 110 and output interface 112. Note that in some embodiments, functionality for one or more of the aforementioned circuits and/or software may be combined into fewer components/modules, or in some embodiments, further distributed among additional components/modules. For instance, the microcontroller 92 may be packaged separately from the ADC 94 and/or the DAC 96. In some embodiments, one or more of the functionality for the above-listed components may be combined.

The sensors 88 are selected to perform detection of one or any combination of different parameters. In one embodiment, the one or more sensors 88 comprise at least motion sensing, including at least a single or multi-axis accelerometer. Motion sensors 88 may further include one or more inertial components, including a gyroscope, magnetometer, etc. The one or more sensors 88 may additionally comprise capabilities for detecting one or more a plurality of physiological parameters, including heart rate, average heart rate, heart rate variation, inter-beat intervals, electrocardiograms (ECGs), heart rate recovery, blood flow rate, etc. In general, the one or more sensors 88 may detect activity level, muscle activity (e.g., movement of limbs, repetitive movement, core movement, body orientation/position, power, speed, acceleration, etc.), muscle tension, blood volume, blood pressure, blood oxygen saturation, respiratory rate, perspiration, skin temperature, body weight, and body composition (e.g., body mass index or BMI). In some embodiments, the sensors 88 may include a photoplethysmographic (PPG) sensor. The sensors 88 may be constructed according to one or more of piezoelectric, piezoresistive or capacitive technology in a microelectromechanical system (MEMS) infrastructure. The sensors 88 may include flex and/or force sensors (e.g., using variable resistance), electromyographic sensors, other types of electrocardiographic sensors (e.g., EKG), magnetic sensors, bio-impedance sensors, infrared proximity sensors, acoustic/ultrasonic/audio sensors, a strain gauge, galvanic skin/sweat sensors, pH sensors, temperature sensors, pressure sensors, and photocells. In some embodiments, other types of sensors 88 may be used, including a global navigation satellite systems (GNSS) sensor (e.g., global positioning system (GPS) receiver, GLONASS receiver, etc.) to facilitate determinations of distance, speed, acceleration, location, altitude, etc. (e.g., location data and movement), barometric pressure, humidity, outdoor temperature, etc. In some embodiments, GNSS functionality may be achieved via components of the communications circuit 108 or other circuits coupled to the microcontroller 92. For instance, GNSS receiver functionality may be replaced with, or augmented by, other position location determination functionality, such as cell tower triangulation, dead-reckoning (e.g., using inertial sensors), among others.

The signal conditioning circuits 90 include amplifiers and filters, among other signal conditioning components, to condition the sensed signals including data corresponding to the sensed physiological and/or motion parameters before further processing is implemented at the microcontroller 92. Though depicted in FIG. 9 as respectively associated with each sensor 88, in some embodiments, fewer signal conditioning circuits 90 may be used (e.g., shared for more than one sensor 88). In some embodiments, the signal conditioning circuits 90 (or functionality thereof) may be incorporated elsewhere, such as in the circuitry of the respective sensors 88 or in the microcontroller 92 (or in components residing therein). Sensing functionality may be achieved via unidirectional signal flow (e.g., from the sensor 88 to the signal conditioning circuit 90 and microcontroller 92) and/or via bi-directional flow. For instance, in the case of optical-based measurements, the microcontroller 92 may cause an optical signal to be emitted from a light source (e.g., light emitting diode(s) or LED(s)) in or coupled to the circuitry of the sensor 88, with the sensor 88 (e.g., photocell) receiving the reflected/refracted signals.

The communications circuit 108 is managed and controlled by the microcontroller 92 (e.g., via instructions of the communications software 106 and/or applications software 104). The communications circuit 108 comprises one or more antennas and known transceiver circuitry to enable wireless/cellular communications according to one or more communications protocols, including GSM, WCDMA, broadband 3G, 4G, 5G, streaming (e.g., LoRa), NFC, BT/BTLE, Wi-Fi/802.11, Zigbee, etc.). In one embodiment, the communications circuit 108 comprises one or more of a wireless modem or cellular modem. In general, the communications circuit 108 is used to communicate with the devices 14 and/or 18 (FIG. 1). As noted above, the communications circuit 108 may comprise cellular capabilities, including via a cellular modem, but for purposes of illustration, is illustrated with BT circuitry that enables communications to the electronics device 14, including using the electronics device 14 as a gateway to communications (e.g., cellular communications) with other devices. In the embodiment depicted in FIG. 9, the communications circuit 108 comprises a transmitter circuit (TX CKT), a switch (SW), an antenna, a receiver circuit (RX CKT), a mixing circuit (MIX), and a frequency hopping controller (HOP CTL). The transmitter circuit and the receiver circuit comprise components suitable for providing respective transmission and reception of an RF signal, including a modulator/demodulator, filters, and amplifiers. In some embodiments, demodulation/modulation and/or filtering may be performed in part or in whole by the processor(s) 98 (e.g., configured as or including digital signal processors in some embodiments). The switch switches between receiving and transmitting modes. The mixing circuit may be embodied as a frequency synthesizer and frequency mixers, as controlled by the microcontroller 92. The frequency hopping controller controls the hopping frequency of a transmitted signal based on feedback from a modulator of the transmitter circuit. In some embodiments, functionality for the frequency hopping controller may be implemented by the microcontroller 92. In some embodiments, the communications circuit 108 may have its own dedicated controller that is supervised and/or managed by the microcontroller 92.

In operation, a signal (e.g., at 2.4 GHz) may be received at the antenna and directed by the switch to the receiver circuit. The receiver circuit, in cooperation with the mixing circuit, converts the received signal into an intermediate frequency (IF) signal under frequency hopping control attributed by the frequency hopping controller and then to baseband for further processing by the ADC. On the transmitting side, the baseband signal (e.g., from the microcontroller 92) is converted to an IF signal and then RF by the transmitter circuit operating in cooperation with the mixing circuit, with the RF signal passed through the switch and emitted from the antenna under frequency hopping control provided by the frequency hopping controller. The modulator and demodulator of the transmitter and receiver circuits may be frequency shift keying (FSK) type modulation/demodulation, though not limited to this type of modulation/demodulation, which enables the conversion between IF and baseband. The memory 100 stores the communications software (or firmware) 106 that is executed by the microcontroller 92 to control the Bluetooth transmission/reception.

Though the communications circuit 108 is depicted as an IF-type transceiver, in some embodiments, a direct conversion architecture may be implemented.

As noted above, the communications circuit 108 may be embodied according to one or more of a plurality of different communication technologies (e.g., GSM, WCDMA, broadband 3G, 4G, 5G, streaming (e.g., LoRa), NFC, BT/BTLE, Wi-Fi/802.11, Zigbee, etc.).

The microcontroller 92 is depicted in FIG. 9 as including the ADC 94 and DAC 96. For sensing functionality, the ADC 94 converts the conditioned signal from the signal conditioning circuit 90 and digitizes the signal for further processing by the microcontroller 92. The ADC 94 may also be used to convert analogs inputs that are received via the input interface 110 to a digital format for further processing by the microcontroller 92. For instance, the ADC 94 may be used to sample a raw or processed signal from the sensor 88 (e.g., configured as an accelerometer). In some embodiments, the signal may be processed by the microcontroller 92, signal conditioning circuit 90, or the sensor 88 to re-orient the axes from that used by the sensor 88 to that used by the microcontroller 92, such that the filtering performed on the samples (e.g., by the signal conditioning circuits 90 or microcontroller 92) is based on sampling a signal either obtained from the accelerometer 88 or derived from the accelerometer 88. The ADC 94 may also be used in baseband processing of signals received via the communications circuit 108. The DAC 96 converts digital information to analog information. Its role for sensing functionality may be to control the emission of signals, such as optical signals or acoustic signal, from the sensors 88. The DAC 96 may further be used to cause the output of analog signals from the output interface 112. Also, the DAC96 may be used to convert the digital information and/or instructions from the microcontroller 92 to analog signal that are fed to the transmitter circuit. In some embodiments, additional conversion circuits may be used.

The one or more processor(s) 98 comprise a hardware device(s) for executing software/firmware, particularly that stored in memory 100. The one or more processor(s) 98 can be any custom made or commercially available processor, a central processing unit (CPU), a multi-core processor, a semiconductor based microprocessor (in the form of a microchip or chip set), a macroprocessor, one or more application specific integrated circuits (ASICs), a plurality of suitably configured digital logic gates, and/or other well-known electrical configurations comprising discrete elements both individually and in various combinations to coordinate the overall operation of the wrist-worn device 12A, or generally any device for executing software instructions. The one or more processor(s) 98 provide for management and control of the wrist-worn device 12A, including processing input from the sensors 88, providing prompts and/or wear location, and for enabling communication with one or more devices 14, 18.

In some embodiments, the one or more of the processors 98 may be configured as a digital signal processor (DSP) that provides for specialized digital signal processing. The DSP may be embodied in specialized integrated circuit(s) or as field programmable gate arrays (FPGAs). In one embodiment, the DSP comprises a pipelined architecture, with comprises a central processing unit (CPU), plural circular buffers and separate program and data memories according to a Harvard architecture. The DSP further comprises dual busses, enabling concurrent instruction and data fetches. The DSP may also comprise an instruction cache and I/O controller. The DSP is generally utilized for math manipulations using registers and math components that may include a multiplier, arithmetic logic unit (ALU, which performs addition, subtraction, absolute value, logical operations, conversion between fixed and floating point units, etc.), and a barrel shifter. The ability of the DSP to implement fast multiply-accumulates (MACs) enables efficient execution of Fast Fourier Transforms (FFTs) and Finite Impulse Response (FIR) filtering. The DSP generally serves an encoding and decoding function in the wrist-worn device 12A. For instance, encoding functionality may involve encoding commands or data corresponding to transfer of information to the devices 14 and/or 18. Also, decoding functionality may involve decoding the information received from the sensors 88 (e.g., after processing by the ADC 94).

The memory 100 may include any one or combination of volatile memory elements (e.g., random access memory (RAM, such as DRAM, SRAM, SDRAM, etc.)) and non-volatile memory elements (e.g., ROM, Flash, solid state, EPROM, EEPROM, etc.). Moreover, the memory 100 may incorporate electronic, magnetic, and/or other types of storage media. The memory 100 may also be referred to herein as a non-transitory, computer readable medium in some embodiments.

The software in memory 100 may include one or more separate programs, each of which comprises an ordered listing of executable instructions for implementing logical functions. The instructions (e.g., executable code) may be in the form of application software, firmware, and/or op-code. In the example of FIG. 9, the software in the memory 100 includes a suitable operating system 102 and the application software 104 that includes one or more algorithms for determining wrist placement of the wrist-worn device 12A. In some embodiments, the application software 104 may further include additional functionality, including fall detection algorithms based on the output from the sensors 88 or additional sensors (e.g., from external sources). The raw or processed data from the sensors 88 may be used by the algorithms to determine wrist-placement and optionally fall prevention/detection. In some embodiments, the application software 104 may provide additional functionality, including the determination of one or more physiological measures (e.g., inter-beat intervals, average heart rate, heart rate variation, electrocardiograms, etc.), and may also be used to derive other parameters. In some embodiments, these derived parameters may be computed externally (e.g., at the devices 14 and/or 18) in lieu of, or in addition to, the computations performed locally at the wrist-worn device 12A. The communications software 106 enables communications with other devices 14 and/or 18, as explained above. The operating system 102 essentially controls the execution of other computer programs, such as the application software 104 and communications software 106, and provides scheduling, input-output control, file and data management, memory management, and communication control and related services. The memory 100 may also include a data structure, which includes user data (e.g., referred to herein also as user-specific information, or user characteristics), such as weight, height, age, gender, body mass index (BMI) that is used by the microcontroller 92 executing the executable code of the algorithms of the application software 104 to accurately interpret the measured physiological and/or motion data. In the context of PERS applications, the memory 100 may be used to store sensor data, contact information (e.g., emergency phone numbers, caregiver phone numbers, family member phone numbers), as well as identifying/address information (e.g., MAC address, SSID) of the wrist-worn device 12A or associated devices. The memory 100 may also store position location information (e.g., GPS coordinates) for one or more locations based on GNSS functionality and associate the information to a designated location (e.g., home or room location or other location where the user commonly resides or visits). In some embodiments, the aforementioned data may be stored elsewhere, such as at the devices 14 and/or 18 in lieu of, or in addition to being stored at the wearable device 12.

The software (e.g., the application software 104, communications software 106, etc.) in memory 100 comprises a source program, executable program (object code), script, or any other entity comprising a set of instructions to be performed. When a source program, then the program may be translated via a compiler, assembler, interpreter, or the like, so as to operate properly in connection with the operating system. Furthermore, the software can be written as (a) an object oriented programming language, which has classes of data and methods, or (b) a procedure programming language, which has routines, subroutines, and/or functions, for example but not limited to, C, C++, Python, Java, among others. The software may be embodied in a computer program product, which may be a non-transitory computer readable medium or other medium.

Execution of the application software 104 may be implemented by the processor(s) 98 under the management and/or control of the operating system 102. The processor(s) 98 may be embodied as a custom-made or commercially available processor, a central processing unit (CPU) or an auxiliary processor among several processors, a semiconductor based microprocessor (in the form of a microchip), a macroprocessor.

The input interface 110 comprises an interface for entry of user input, such as a button (e.g., fall alert button) or microphone or sensor (e.g., to detect user input). The input interface 110 may serve as a communications port for downloaded information to the wrist-worn device 12A (such as via a wired connection). The output interfaces 112 comprise one or more interfaces for the presentation (e.g., prompts, including alerts) or transfer of data, such as a display screen, speaker, and/or communications interface for the transfer (e.g., wired) of information stored in the memory, or to enable one or more feedback devices, such as lighting devices (e.g., LEDs), audio devices (e.g., tone generator and speaker), and/or tactile feedback devices (e.g., vibratory motor). In some embodiments, at least some of the functionality of the input and output interfaces 110 and 112, respectively, may be combined, such as in the case of a touch-type display screen. The wrist-worn device 12A also comprises a power (POWER) module, such as a (rechargeable) battery or other source of power.

When certain embodiments of the wrist-worn device 12A are implemented at least in part with software (including firmware), as depicted in FIG. 9, it should be noted that the software (e.g., such as the application software 104) can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the wrist-worn device 12A are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 10:
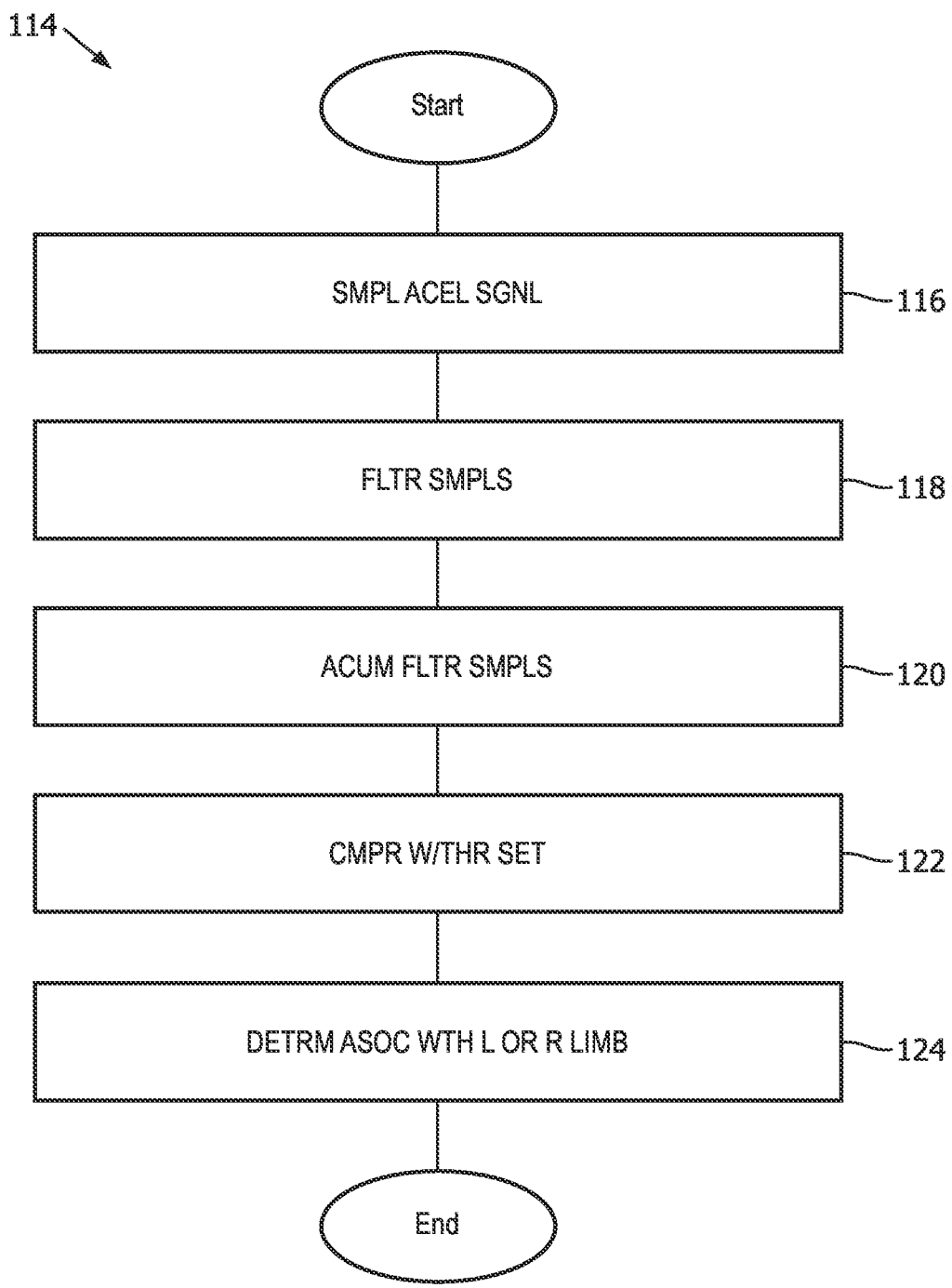
FIG. 10 is a flow diagram that illustrates an example method for determining left or right limb placement of an apparatus, in accordance with an embodiment of the invention.

In view of the description above, it should be appreciated that one embodiment of a method, depicted in FIG. 10 and referred to as method 114 and in one embodiment, implemented in an apparatus (e.g., wrist-worn device 12A), comprises sampling a signal obtained or derived from an accelerometer (116); filtering the samples according to at least a first threshold (118); accumulating the filtered samples over a period of time, each of the accumulated filtered samples comprising a respective sub-value ($a_x$) that collectively comprise a first value over the period of time (120); comparing the first value with a threshold set (122); and determining that the apparatus is either associated with a left limb or a right limb based on the comparison (124). In some embodiments, the signal comprises a raw or processed signal (e.g., including re-orienting the axes via signal rotation) that is digitized/sampled and then filtered according to one or more thresholds. The accumulated, filtered samples may include in some embodiments, normalization. In some embodiments, more than one value may result from accumulating multiple sets of sub-samples. Note that the accelerator may be calibrated in some embodiments, or un-calibrated in some embodiments.

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure.

In one embodiment, an apparatus is disclosed, comprising: an accelerometer; a memory comprising instructions; and a processor configured by the instructions to: sample a signal obtained or derived from the accelerometer; filter the samples according to at least a first threshold; accumulate the filtered samples over a period of time, each of the accumulated filtered samples comprising a respective sub-value that collectively comprise a first value over the period of time; compare the first value with a threshold set; and determine that the apparatus is either associated with a left limb or a right limb based on the comparison.

In one embodiment, the preceding apparatus, wherein the processor is further configured by the instructions to: determine that the apparatus is associated with the right limb when the first value exceeds a second threshold of the threshold set; and determine that the apparatus is associated with the left limb when the first value falls below a third threshold of the threshold set.

In one embodiment, any one of the preceding apparatuses, wherein the processor is further configured by the instructions to obtain or derive the signal from a single axis of the accelerometer and determine placement based on the first value and a polarity of the first value.

In one embodiment, any one of the preceding apparatuses, wherein the processor is further configured by the instructions to isolate distribution tails of the signal obtained or derived from the accelerometer via the filtering based on the at least first threshold, wherein the at least first threshold corresponds to a gravitational norm value plus a predefined margin.

In one embodiment, any one of the preceding apparatuses, wherein the processor is further configured by the instructions to filter the samples according further to a fourth threshold, wherein each sample that is greater than the first threshold and less than the fourth threshold comprises one of the accumulated filtered samples.

In one embodiment, any one of the preceding apparatuses, wherein the period of time comprises a predefined duration and the threshold set comprises a positive value and a negative value of a predefined acceleration value, or a single value and a sign component.

In one embodiment, the preceding apparatus, wherein the period of time, the at least first threshold, and the threshold set are derived based on a training period having a duration of greater than a day.

In one embodiment, any one of the preceding apparatuses, wherein the processor is further configured by the instructions to update the first value as the filtered samples each comprising the respective sub-value are accumulated.

In one embodiment, the preceding apparatus, wherein the processor is further configured by the instructions to: update the first value only during periods of activity; and detect the periods of activity based on one of an average standard deviation of three axes of the accelerometer or a standard deviation of one axis of the accelerometer.

In one embodiment, the preceding apparatus, further comprising one or more additional sensors, wherein prior to the activity detection, the processor is further configured by the instructions to detect that the apparatus is being worn or carried based on receiving a signal or signals from the one or more additional sensors.

In one embodiment, the preceding apparatus, further comprising a user interface, wherein the processor is further configured by the instructions to: determine that the location of the apparatus has changed; and prompt a user to provide an indication of whether the apparatus is associated with the left limb or the right limb.

In one embodiment, any one of the preceding apparatuses, wherein the apparatus comprises a wrist-worn device, and wherein the accumulated samples are for a single axis of the accelerometer, wherein the processor is further configured by the instructions to: determine that the wrist-worn device is either located on a left wrist or a right wrist when a watchcase of the wrist-worn device is rotated by accumulating additional samples from another axis of the accelerometer to derive a second value and comparing signs of the first and second values; and determine the location of the wrist-worn device based on whether the signs are equal or not equal.

In one embodiment, any one of the preceding apparatuses, wherein the processor is further configured by the instructions to accumulate the samples as the first value and accumulate additional filtered samples collectively comprising a second value, the second value based on a plurality of second sub-value, the first and second value associated with first and second counters corresponding respectively to left and right limb-derived samples that are incremented by one when a respective sample is greater than the first threshold and less than a negative of the first threshold, the processor further configured by the instructions to compare the first and second values with the threshold set by computing a ratio measure based on the first and second counters and comparing the ratio measure with the threshold set.

In one embodiment, a method is disclosed for determining whether any one of the preceding apparatuses is associated with the left limb or the right limb of a user.

In one embodiment, a non-transitory computer readable medium is disclosed comprising the instructions that, when executed by the processor, causes the processor to implement the preceding method.

Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:

1. A wrist-worn apparatus configured to be interchangeably worn on a user's left limb or the user's right limb, comprising:
   an accelerometer configured to generate a signal indicative of movement by the user of the limb on which the wrist-worn apparatus is worn;
   a memory comprising instructions;
   a processor configured to execute the instructions to:
      sample the signal obtained or derived from the accelerometer to generate a plurality of accelerometer samples, each of the plurality of accelerometer samples comprising a respective sub-value;
      compare each of the plurality of accelerometer samples to a first threshold of a threshold set, and only retaining those of the compared plurality of accelerometer samples that exceed the first threshold, wherein the first threshold is configured such that the retained plurality of accelerometer samples are isolated distribution tails of the signal obtained or derived from the accelerometer, and wherein the first threshold corresponds to a gravitational norm value plus a predefined margin;
      accumulate the retained samples over a period of time the respective sub-values of the accumulated retained samples collectively comprising a first value over the period of time;
      compare the first value with a second threshold and a third threshold of the threshold set; and
      determine that the apparatus is either associated with a left limb or a right limb based on the comparison, wherein the apparatus is associated with the right limb when the first value exceeds the second threshold of the threshold set, and wherein the apparatus is associated with the left limb when the first value falls below the third threshold of the threshold set; and a display configured to provide the determination that the apparatus is either associated with a left limb or a right limb.

2. The apparatus of claim 1, wherein the processor is further configured to execute the instructions to obtain or derive the signal from a single axis of the accelerometer and determine placement based on the first value and a polarity of the first value.

3. The apparatus of claim 1, wherein the processor is further configured to execute the instructions to filter the samples according further to a fourth threshold, wherein each sample that is greater than the first threshold and less than the fourth threshold comprises one of the accumulated filtered samples.

4. The apparatus of claim 1, wherein the period of time comprises a predefined duration and the threshold set comprises a positive value and a negative value of a predefined acceleration value, or a single value and a sign component.

5. The apparatus of claim 4, wherein the period of time, the at least first threshold, and the threshold set are derived based on a training period having a duration of greater than a day.

6. The apparatus of claim 1, wherein the processor is further configured to execute the instructions to update the first value as the filtered samples each comprising the respective sub-value are accumulated.

7. The apparatus of claim 6, wherein the processor is further configured to execute the instructions to:
update the first value only during periods of activity; and
detect the periods of activity based on one of an average standard deviation of three axes of the accelerometer or a standard deviation of one axis of the accelerometer.

8. The apparatus of claim 7, further comprising one or more additional sensors, wherein prior to the activity detection, the processor is further configured to execute the instructions to detect that the apparatus is being worn or carried based on receiving a signal or signals from the one or more additional sensors.

9. The apparatus of claim 8, wherein the processor is further configured to execute the instructions to:
determine that the location of the apparatus has changed; and
prompt a user, via the display, to provide an indication of whether the apparatus is associated with the left limb or the right limb.

10. The apparatus of claim 1, wherein the apparatus comprises a wrist-worn device, and wherein the accumulated samples are for a single axis of the accelerometer, wherein the processor is further configured to execute the instructions to:
determine that the wrist-worn device is either located on a left wrist or a right wrist when a watchcase of the wrist-worn device is rotated by accumulating additional samples from another axis of the accelerometer to derive a second value and comparing signs of the first and second values; and
determine the location of the wrist-worn device based on whether the signs are equal or not equal.

11. The apparatus of claim 1, wherein the processor is further configured to execute the instructions to accumulate the samples as the first value and accumulate additional filtered samples collectively comprising a second value, the second value based on a plurality of second sub-value, the first and second value associated with first and second counters corresponding respectively to left and right limb-derived samples that are incremented by one when a respective sample is greater than the first threshold and less than a negative of the first threshold, the processor further configured to execute the instructions to compare the first and second values with the threshold set by computing a ratio measure based on the first and second counters and comparing the ratio measure with the threshold set.

12. A method for determining whether a wrist-worn apparatus is associated with a left limb or a right limb of a user, comprising:
providing a wrist-worn apparatus configured to be interchangeably worn on a user's left limb or the user's right limb, the wrist-worn apparatus comprising: (i) an accelerometer configured to generate a signal indicative of movement by the user of the limb on which the wrist-worn apparatus is worn; (ii) a memory comprising instructions; (iii) a processor; and (iv) a display;
sampling, by the processor, the signal obtained or derived from the accelerometer to generate a plurality of accelerometer samples, each of the plurality of accelerometer samples comprising a respective sub-value;
comparing, by the processor, each of the plurality of accelerometer samples to a first threshold of a threshold set, and only retaining those of the compared plurality of accelerometer samples that exceed the first threshold, wherein the first threshold is configured such that the retained plurality of accelerometer samples are isolated distribution tails of the signal obtained or derived from the accelerometer, and wherein the first threshold corresponds to a gravitational norm value plus a predefined margin;
accumulating, by the processor, the retained samples over a period of time, the respective sub-values of the accumulated retained samples collectively comprising a first value over the period of time;
comparing, by the processor, the first value with a second threshold and a third threshold of the threshold set;
determining, by the processor, that the apparatus is either associated with a left limb or a right limb based on the comparison, wherein the apparatus is associated with the right limb when the first value exceeds the second threshold of the threshold set, and wherein the apparatus is associated with the left limb when the first value falls below the third threshold of the threshold set; and
providing, via the display, the determination that the apparatus is either associated with a left limb or a right limb.

* * * * *